(12) United States Patent
Yamada

(10) Patent No.: US 10,485,505 B2
(45) Date of Patent: Nov. 26, 2019

(54) RADIOGRAPHING APPARATUS, CONTROL APPARATUS, STITCH IMAGING SYSTEM, CONTROL METHOD

(71) Applicant: CANON KABUSHIKI KAISHA, Tokyo (JP)

(72) Inventor: Daisuke Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 322 days.

(21) Appl. No.: 15/011,046

(22) Filed: Jan. 29, 2016

(65) Prior Publication Data

US 2016/0220211 A1    Aug. 4, 2016

(30) Foreign Application Priority Data

Jan. 30, 2015    (JP) .................. 2015-017885

(51) Int. Cl.
*A61B 6/00*    (2006.01)

(52) U.S. Cl.
CPC .............. *A61B 6/5241* (2013.01); *A61B 6/42* (2013.01); *A61B 6/4208* (2013.01);
(Continued)

(58) Field of Classification Search
CPC ... A61B 6/4208; A61B 6/4266; A61B 6/5235; A61B 6/5241; A61B 6/54; A61B 6/542; A61B 6/56; A61B 6/563; A61B 6/566; A61B 6/42; A61B 6/52; A61B 6/5205; A61B 6/5211; A61B 6/5229
(Continued)

(56) References Cited

U.S. PATENT DOCUMENTS

| 6,215,848 B1 * | 4/2001 | Linders | A61B 6/481 |
| | | | 250/370.09 |
| 6,273,606 B1 * | 8/2001 | Dewaele | A61B 6/5241 |
| | | | 378/174 |

(Continued)

FOREIGN PATENT DOCUMENTS

| CN | 101176670 A | 5/2008 |
| JP | 2005-257634 A | 9/2005 |

(Continued)

*Primary Examiner* — Allen C. Ho
(74) *Attorney, Agent, or Firm* — Canon U.S.A., Inc. IP Division

(57) ABSTRACT

A radiographing apparatus usable for stitch imaging, includes a radiation sensor configured to acquire a radiographic image signal or radiographic image signals by detecting radiation, a readout circuit configured to read out the radiographic image signal(s), a communication circuit configured to transmit a digital radiographic image based on the radiographic image signal(s) to an external apparatus, a generation unit configured to generate a preview image, based on the radiographic image signal(s), that is smaller in data amount than the digital radiographic image, and a control unit configured to cause the communication circuit to start transmitting the preview image after the readout circuit reads out the radiographic image signal(s), and after completion of the transmission of the preview image, restrict transmission of an image that contains data uncontained in the preview image among data pieces in the digital radiographic image until a specific signal is received from the external apparatus.

21 Claims, 13 Drawing Sheets

(52) U.S. Cl.
CPC .............. *A61B 6/4266* (2013.01); *A61B 6/52* (2013.01); *A61B 6/5205* (2013.01); *A61B 6/5211* (2013.01); *A61B 6/5229* (2013.01); *A61B 6/5235* (2013.01); *A61B 6/54* (2013.01); *A61B 6/542* (2013.01); *A61B 6/56* (2013.01); *A61B 6/563* (2013.01); *A61B 6/566* (2013.01)

(58) Field of Classification Search
USPC ...................... 378/62, 98.12, 98.8
See application file for complete search history.

(56) References Cited

U.S. PATENT DOCUMENTS

| | | | | |
|---|---|---|---|---|
| 6,463,121 B1* | 10/2002 | Milnes | .................. | A61B 6/4482 378/62 |
| 6,793,390 B2* | 9/2004 | Wang | .................... | G06T 3/0075 378/174 |
| 6,895,106 B2* | 5/2005 | Wang | .................... | A61B 6/5241 382/132 |
| 7,103,138 B2* | 9/2006 | Pelc | ........................ | A61B 6/032 378/4 |
| 7,197,529 B2* | 3/2007 | Nakagawa | ............ | A61B 6/4216 378/167 |
| 7,250,608 B2* | 7/2007 | Ozeki | .................... | G01T 1/2018 250/370.01 |
| 7,265,355 B2* | 9/2007 | Chang | ................... | A61B 6/5241 250/370.09 |
| 7,408,166 B2* | 8/2008 | Schafer | .................... | H04N 5/32 250/370.09 |
| 7,498,583 B2* | 3/2009 | Shoji | ..................... | A61B 6/4266 250/370.09 |
| 7,522,701 B2* | 4/2009 | Jensen | .................. | A61B 6/481 378/162 |
| 7,555,100 B2* | 6/2009 | Wang | ...................... | A61B 6/02 378/98.12 |
| 7,558,438 B1 | 7/2009 | Sasada | | |
| 7,608,836 B2* | 10/2009 | Wieczorek | ............ | G01T 1/2018 250/370.11 |
| 7,751,529 B2* | 7/2010 | Ohara | ...................... | A61B 6/00 378/116 |
| 7,974,382 B2* | 7/2011 | Kitano | ................... | G01N 23/04 378/114 |
| 8,021,047 B2* | 9/2011 | Yoshida | ............... | A61B 6/4035 378/114 |
| 8,108,432 B2* | 1/2012 | Westin | ............... | G06F 17/3028 707/792 |
| 8,199,880 B2* | 6/2012 | Yamada | .................... | A61B 6/00 378/114 |
| 8,213,572 B2* | 7/2012 | Minnigh | .................. | A61B 6/06 378/145 |
| 8,223,922 B2* | 7/2012 | Suyama | ................ | G01N 23/04 378/98.9 |
| 8,280,005 B2* | 10/2012 | Suyama | ................... | G01T 1/00 250/370.09 |
| 8,295,434 B2* | 10/2012 | Boese | ...................... | A61B 6/06 378/62 |
| 8,340,246 B2* | 12/2012 | Kang | ...................... | A61B 6/06 378/146 |
| 8,344,327 B2* | 1/2013 | Yamaguchi | .......... | A61B 6/5241 250/363.07 |
| 8,351,568 B2* | 1/2013 | Minnigh | ................ | A61B 6/4266 378/204 |
| 8,360,639 B2* | 1/2013 | Kato | .................... | A61B 6/4233 378/197 |
| 8,461,543 B2* | 6/2013 | Nishino | ................. | A61B 6/548 250/370.08 |
| 8,586,934 B2* | 11/2013 | Nakatsugawa | ....... | G01T 1/2985 250/370.08 |
| 8,625,742 B2* | 1/2014 | Iwashita | ............... | A61B 6/4266 378/116 |
| 8,731,141 B2* | 5/2014 | Kuwabara | .............. | A61B 6/00 378/116 |
| 8,748,834 B2* | 6/2014 | Enomoto | ............. | A61B 6/4233 250/370.08 |
| 8,899,832 B2* | 12/2014 | Fabrizio | .................. | A61B 6/08 378/195 |
| 8,942,444 B2* | 1/2015 | Liu | ........................ | A61B 6/563 128/922 |
| 9,001,972 B2* | 4/2015 | Takahashi | ................ | H05G 1/30 378/62 |
| 9,016,940 B2* | 4/2015 | Fabrizio | .................. | A61B 6/02 378/177 |
| 9,050,023 B2* | 6/2015 | Okuno | .................... | A61B 6/08 |
| 9,078,620 B2* | 7/2015 | Shin | ..................... | A61B 6/4452 |
| 9,121,809 B2* | 9/2015 | Cox | ....................... | G01N 23/04 |
| 9,131,905 B2* | 9/2015 | Abe | ........................ | A61B 6/00 |
| 9,149,247 B2* | 10/2015 | Lee | ...................... | A61B 6/4452 |
| 9,155,507 B2* | 10/2015 | Behiels | ................ | A61B 6/5229 |
| 9,168,011 B2* | 10/2015 | Nenoki | .................. | A61B 6/4283 |
| 9,204,937 B2* | 12/2015 | Edelhauser | ............ | A61B 17/62 |
| 9,216,006 B2* | 12/2015 | Kuwabara | ............. | A61B 6/4233 |
| 9,265,467 B2* | 2/2016 | Kamiya | ................ | A61B 6/5241 |
| 9,355,437 B2* | 5/2016 | Lou | ......................... | G06T 5/006 |
| 9,357,974 B2* | 6/2016 | Foos | .................... | A61B 6/4405 |
| 9,395,450 B2* | 7/2016 | Tezuka | .................. | H04N 5/2176 |
| 9,398,887 B2* | 7/2016 | Miyazawa | ............. | A61B 6/463 |
| 9,405,183 B2* | 8/2016 | Ando | ................... | A61B 6/4266 |
| 9,407,922 B2* | 8/2016 | Maruo | .................. | G06F 19/321 |
| 9,498,173 B2* | 11/2016 | Yamada | ................ | A61B 6/4405 |
| 9,521,986 B2* | 12/2016 | Ozawa | .................. | A61B 6/4283 |
| 9,536,045 B1* | 1/2017 | Fram | ......................... | G06T 9/00 |
| 9,536,501 B2* | 1/2017 | Takeda | .................... | A61B 6/52 |
| 9,541,509 B2* | 1/2017 | Akahori | ................. | A61B 6/486 |
| 9,554,762 B2* | 1/2017 | Kim | ......................... | A61B 6/48 |
| 9,569,829 B2* | 2/2017 | Ohguri | ................... | H04N 5/2254 |
| 9,582,152 B2* | 2/2017 | Gulaka | ................ | G06F 3/04845 |
| 9,597,049 B2* | 3/2017 | Li | ............................ | G06Q 50/24 |
| 9,610,053 B2* | 4/2017 | Okuno | ..................... | A61B 6/40 |
| 9,646,649 B2* | 5/2017 | Sugawara | ............ | G11B 27/036 |
| 9,649,086 B2* | 5/2017 | Tajima | .................... | A61B 6/563 |
| 9,661,728 B2* | 5/2017 | Eguchi | ..................... | H05G 1/08 |
| 9,662,083 B2* | 5/2017 | Sakaue | ................. | A61B 6/5247 |
| 9,665,254 B2* | 5/2017 | Hayashi | .................. | A61B 6/463 |
| 9,665,918 B2* | 5/2017 | Ohyu | .................... | G06Q 50/22 |
| 9,675,309 B2* | 6/2017 | Kim | .................... | A61B 6/4266 |
| 9,690,902 B2* | 6/2017 | Arakita | ................. | G06F 19/321 |
| 9,697,923 B2* | 7/2017 | Tsuji | ................... | A61B 6/4266 |
| 9,700,270 B2* | 7/2017 | Tateishi | ............... | A61B 6/4266 |
| 9,700,274 B2* | 7/2017 | Aoyagi | .................. | A61B 6/463 |
| 9,700,278 B2* | 7/2017 | Tezuka | .................. | A61B 6/563 |
| 9,728,001 B2* | 8/2017 | Koenig | ................... | G06T 15/40 |
| 9,757,086 B2* | 9/2017 | Tezuka | .................... | A61B 6/54 |
| 9,782,144 B2* | 10/2017 | Kuwabara | ............ | A61B 6/566 |
| 9,786,051 B2* | 10/2017 | Harper | ................... | G06T 7/0014 |
| 9,788,809 B2* | 10/2017 | Hiroike | ................. | A61B 6/4233 |
| 9,801,596 B2* | 10/2017 | Tagawa | ................. | A61B 6/4233 |
| 9,805,161 B2* | 10/2017 | Hoshino | ................ | G06F 19/322 |
| 9,814,435 B2* | 11/2017 | Kim | ....................... | A61B 6/469 |
| 9,820,703 B2* | 11/2017 | Wojcik | .................. | A61B 6/4233 |
| 9,861,334 B2* | 1/2018 | Tajima | .................... | A61B 6/5294 |
| 9,875,256 B2* | 1/2018 | Takata | .................... | G16H 50/70 |
| 9,888,900 B2* | 2/2018 | Tachikawa | ............. | A61B 6/542 |
| 9,931,092 B2* | 4/2018 | Tajima | .................... | A61B 6/488 |
| 9,949,707 B2* | 4/2018 | Miyachi | ................ | A61B 6/5241 |
| 10,104,311 B2* | 10/2018 | Takekoshi | ............ | A61B 6/5241 |
| 2004/0120457 A1* | 6/2004 | Karellas | ................... | A61B 6/06 378/62 |
| 2008/0107234 A1 | 5/2008 | Amitani | | |
| 2011/0057111 A1 | 3/2011 | Nishino | | |
| 2011/0064193 A1 | 3/2011 | Minnigh et al. | | |
| 2011/0233415 A1 | 9/2011 | Nakatsugawa et al. | | |
| 2011/0286582 A1 | 11/2011 | Iwashita et al. | | |
| 2012/0049080 A1 | 3/2012 | Enomoto | | |
| 2013/0121471 A1 | 5/2013 | Takahashi et al. | | |
| 2014/0239188 A1 | 8/2014 | Tezuka | | |

FOREIGN PATENT DOCUMENTS

| | | |
|---|---|---|
| JP | 2011-004856 A | 1/2011 |
| JP | 2011-224338 A | 11/2011 |

(56) References Cited

FOREIGN PATENT DOCUMENTS

| JP | 2011-227047 A | 11/2011 |
|----|---------------|---------|
| JP | 2012-045172 A | 3/2012 |
| JP | 2013-226243 A | 11/2013 |
| JP | 2016059534 A | 4/2016 |

* cited by examiner

RADIOGRAPHING APPARATUS, CONTROL APPARATUS, STITCH IMAGING SYSTEM, CONTROL METHOD

BACKGROUND OF THE INVENTION

Field of the Invention

The present invention relates to a radiographing system using a plurality of radiographic imaging units.

Description of the Related Art

As one of photographing methods using a radiographic imaging unit, such as a film cassette, an imaging plate based on the Computed Radiography (CR) method, or a digital radiation detector, there is stitch imaging for capturing a larger subject than a region where a single radiographic imaging unit detects radiation.

Methods for implementing the stitch imaging include a method that lays out a plurality of radiographic imaging units and irradiates the subject with a single shot of radiation, besides a method that irradiates the subject with a plurality of shots of radiation while moving a single radiographic imaging unit. A plurality of radiographic images acquired by any of these methods is appropriately arranged and stitched, by which an image of the larger subject than the region where the single radiographic imaging unit detects radiation can be acquired.

Processing for receiving the images from the individual radiographic imaging units and processing for stitching these images are required to acquire the stitched image from the stitch imaging using the plurality of radiographic imaging units and display this stitched image. However, these processing procedures take a long time. The radiographic imaging faces the demands for allowing the image to be quickly checked after the photography, and reducing a time for which the subject is kept detained for the photography.

SUMMARY OF THE INVENTION

According to an aspect of the present invention, a radiographing apparatus usable for stitch imaging, includes a radiation sensor configured to acquire a radiographic image signal or radiographic image signals by detecting radiation, a readout circuit configured to read out the radiographic image signal(s), a communication circuit configured to transmit a digital radiographic image based on the radiographic image signal(s) to an external apparatus, a generation unit configured to generate a preview image, based on the radiographic image signal(s), that is smaller in data amount than the digital radiographic image, and a control unit configured to cause the communication circuit to start transmitting the preview image after the readout circuit reads out the radiographic image signal(s), and after completion of the transmission of the preview image, restrict transmission of an image that contains data uncontained in the preview image among data pieces in the digital radiographic image until a specific signal is received from the external apparatus.

Further features of the present invention will become apparent from the following description of exemplary embodiments with reference to the attached drawings.

DESCRIPTION OF THE EMBODIMENTS

Figure 1:
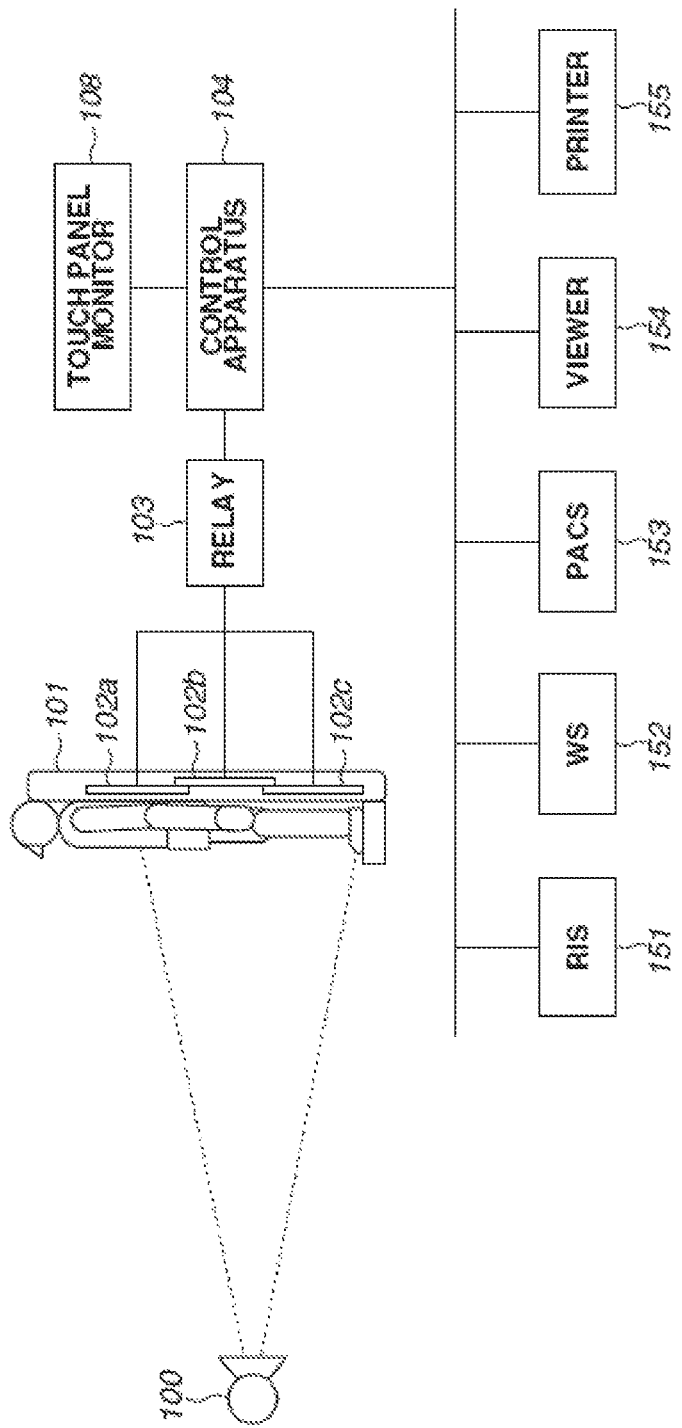
FIG. 1 is a block diagram illustrating a configuration of an information system including a radiographing system according to an exemplary embodiment.

A radiographing system according to an exemplary embodiment will be described with reference to FIG. 1. FIG. 1 illustrates a configuration of an information system including a stitch imaging system using an X-ray as radiation, which is an example of the radiographing system. This information system includes, for example, the radiographing system, a radiology information system (RIS) 151, a workstation (WS) 152, a picture archiving and communication system (PACS) 153, a viewer 154, and a printer 155. The RIS 151 is a system that manages an order for radiographic imaging, and transmits the order for radiographic imaging to the radiographing system. The WS 152 is an image processing terminal, and processes a radiographic image captured by the radiographing system to acquire an image for use in diagnosis. The PACS 153 is a database system that contains medical images provided from the radiographing system and another modality (a medical imaging system or a medial image-capturing apparatus). The PACS 153 includes a storage unit that stores the medical images and appendant information, such as image-capturing conditions applied for these medical images, and a controller that manages the information stored in this storage unit. The viewer 154 is a terminal for use in image diagnosis, and reads out the image stored in the PACS 153 or the like to display this image for the diagnosis. The printer 155 is, for example, a film printer, and outputs the image stored in the PACS 153 onto a film.

The stitch imaging system, which is an example of the radiographing system, includes a radiation generation unit 100, a platform 101, a plurality of radiographic imaging units 102a, 102b, and 102c (or a cassette A, a cassette B, and a cassette C), a relay 103, a control apparatus 104, and a touch panel monitor 108 that serves as both a display unit and an operation unit. These components are connected to one another via a cable. The radiation generation unit 100 emits the radiation to the plurality of radiographic imaging units 102a, 102b, and 102c simultaneously for irradiation. When the radiation is emitted to the plurality of radiographic imaging units 102a, 102b, and 102c for the irradiation, the plurality of radiographic imaging units 102a, 102b, and 102c acquires radiographic images, and this plurality of radiographic images is transmitted to the control apparatus 104 via the relay 103.

The control apparatus 104 is, for example, an electronic computer (a personal computer (PC)) with a desired software program installed therein, and generates a stitched image by performing image processing including stitching processing on this plurality of radiographic images. Further, the control apparatus 104 causes this stitched image to be displayed on the touch panel monitor 108. In this manner, the stitch imaging system carries out the stitch imaging of emitting the radiation to the plurality of radiographic imaging units 102a, 102b, and 102c simultaneously for the irradiation. Further, the control apparatus 104 generates a Digital Imaging and Communications in Medicine (DICOM) image based on this stitched image and appendant information, such as an image-capturing condition applied for this stitched image. Then, the control apparatus 104 transmits this DICOM image to the WS 152 or the PACS 153.

A photography order for the stitch imaging is, for example, transmitted from the RIS 151 to the control apparatus 104. In this case, the control apparatus 104 receives, from the RIS 151, a photography information identification (ID) indicating the stitch imaging, and information indicating an image-capturing site that should be photographed by the stitch imaging, such as an entire lower limb and an entire spine, and reads out an image-capturing condition corresponding to this received information from a storage unit of the control apparatus 104. Alternatively, the control apparatus 104 may be assumed to acquire photography information including information indicating the image-capturing site, a photography method, and the image-capturing condition from an operation input via the touch panel monitor 108.

Besides the touch panel monitor 108, an operation unit such as a mouse and a keyboard may be connected to the control apparatus 104.

As illustrated in FIG. 1, the radiographic imaging units 102a, 102b, and 102c (hereinafter, collectively referred to as radiographic imaging units 102) are laid out in such a manner that a region that the radiographic imaging unit 102a captures and a region that the radiographic imaging unit 102b captures partially overlap each other so as to establish a continuous imaging region. This layout results in the appearance of a predetermined structure in the radiographic image acquired by the radiographic imaging unit 102b. On the platform 101 according to the present exemplary embodiment, only a radiographic imaging unit 102 disposed in the middle among the radiographic imaging units 102a, 102b, and 102c disposed in the order is located at a position farther away from the radiation generation unit 100 than the other radiographic imaging units 102, and is arranged in such a manner that the imaging region thereof partially overlaps the imaging regions of the other radiographic imaging units 102. Laying out the radiographic imaging units 102a, 102b, and 102c in this manner can reduce the number of radiographic images with the structure appearing therein.

The radiographic image with the structure appearing therein is corrected by, for example, the control apparatus 104 or the radiographic imaging unit 102 with use of correction data for correcting the structure that is separately acquired, so that the number of structures appearing in the radiographic image(s) is reduced.

A configuration of the stitch imaging system according to the present exemplary embodiment will be described in detail with reference to FIG. 2. The radiation generation unit 100 includes a radiation irradiation unit 100a that includes a diaphragm for setting a range to be irradiated with the radiation and a radiation source for generating the radiation, and a generation control unit 100b for controlling the irradiation with the radiation by the radiation irradiation unit 100a. An irradiation switch is further connected to the generation control unit 100b to input a signal for instructing the generation control unit 100b about a timing of starting the irradiation to the generation control unit 100b. The radiation generation unit 100 may further include an interface unit 203 that communicates with the radiographic imaging units 102a, 102b, and 102c. In this case, the radiation generation unit 100 and the platform 101 are connected communicably with each other via a network cable 205e, such as an Ethernet (registered trademark) cable. The control apparatus 104 is connected to the platform 101 communicably with each other via a network cable 205d.

The platform 101 is a holder unit that fixes the plurality of radiographic imaging units 102a, 102b, and 102c for carrying out the stitch imaging. In one exemplary embodiment, the platform 101 has three positions for fixing the radiographic imaging units 102a, 102b, and 102c, and includes a housing portion 201 (i.e., 201a, 201b, and 201c) that houses the radiographic imaging unit 102, and a platform connector 206 (i.e., 206a, 206b, and 206c) at each of the fixation positions. The position of each of the connectors 206 is determined in such a manner that the platform connector 206 and a radiographic imaging unit connector 107 (i.e., 107a, 107b, and 107c) are fitted to each other when the radiographic imaging unit 102 is fixed in the housing portion 201.

The platform 101 includes housing portions 201a, 201b, and 201c that house the radiographic imaging units 102a, 102b, and 102c, respectively, platform connectors 206a, 206b, and 206c respectively disposed along sidewalls of the housing portions 201a, 201b, and 201c and respectively provided for establishing wired connections with the radiographic imaging units 102a, 102b, and 102c, and the relay 103 (a network switch).

The platform connectors 206a, 206b, and 206c are connected to the relay 103 via network cables 205a, 205b, and 205c, respectively. Further, the platform connectors 206a, 206b, and 206c are connected to the radiographic imaging unit connectors 107 of the radiographic imaging units 102a, 102b, and 102c, respectively. In the example illustrated in FIG. 2, a radiographic imaging unit connector 107b of the radiographic imaging unit 102b, a radiographic imaging unit connector 107c of the radiographic imaging unit 102c, and a radiographic imaging unit connector 107a of the radiographic imaging unit 102a are connected to the platform connector 206a, the platform connector 206b, and the platform connector 206c, respectively.

The relay 103 is the network switch, and one of a plurality of physical ports thereof is extended out of the platform 101 so as to be connectable to the control apparatus 104. This port is fixedly wired so as to be connected to a communication port of the control apparatus 104, when the platform 101 and the control apparatus 104 are set up in a user's use environment. The remaining ports are wired so as to be connected to the platform connectors 206a, 206b, and 206c at the cassette fixation positions. This wiring is fixedly wired when the platform 101 is manufactured, so that corresponding relationships between the platform connectors 206a, 206b, and 206c and the physical ports of the relay 103 do not change over the course of the user's use.

The platform 101 may further include a power source 207 that supplies power to the radiographic imaging units 102a, 102b, and 102c. This configuration leads to connections of two cable systems, a network cable and a power source cable to each of the platform connectors 206a, 206b, and 206c. Instead of the power source unit 207, power source units 202a, 202b, and 202c may be provided with respect to the housing portions 201a, 201b, and 201c, respectively. This configuration leads to connections of two systems, a communication cable and a power source cable between the platform connector 206 and the power source unit 202, and a connection of a communication cable between the power source unit 202 and the relay 103.

The radiographic images provided from the radiographic imaging units 102a, 102b, and 102c are transmitted to the control apparatus 104 via the radiographic imaging unit connectors 107a, 107b, and 107c, the platform connectors 206a, 206b, and 206c, and the relay 103.

In another exemplary embodiment, the platform 101 may be configured to include a radiographic imaging unit connection unit and a platform connection unit that perform near field wireless communication, such as TransferJet, instead of the radiographic imaging unit connector 107 and the platform connector 206. Alternatively, the radiographic imaging unit 102 may be configured to wirelessly communicate with the relay 103 directly without communicating via the platform connector 206 and the like. This configuration leads to the radiographic imaging unit 102 wirelessly communicating with the platform 101 and the relay 103, and makes the communication path partially wireless between the radiographic imaging unit 102 and the control apparatus 104.

The relay 103 is disposed inside the platform 101, but is not limited thereto and may be disposed outside the platform 101. Further, the relay 103 and the radiation generation unit 100 may be connected to each other via a wireless communication path, and the relay 103 and the control apparatus 104 may be connected to each other via a wireless communication path.

To carry out the stitch imaging, first, the radiographic imaging units 102a, 102b, and 102c are fixedly mounted onto the respective fixation positions of the platform 101 provided for the stitch imaging. By this mounting, the platform connectors 206a, 206b, and 206c and the radiographic imaging unit connectors 107a, 107b, and 107c are fitted to each other, respectively. By this fitting, respective main control circuits inside the individual radiographic imaging units 102a, 102b, and 102c are connected to the relay 103 via the radiographic imaging unit connectors 107a, 107b, and 107c, the platform connectors 206a, 206b, and 206c, and the network cables 205a, 205b, and 205c, respectively. As a result, a network including the individual radiographic imaging units 102a, 102b, and 102c and the control apparatus 104 is created. The radiographic imaging units 102a, 102b, and 102c and the relay 103 are connected in an individually attachable and detachable manner by the fitted attachment between the radiographic imaging unit connectors 107a, 107b, and 107c and the platform connectors 206a, 206b, and 206c.

The creation of the network allows each of the cassettes A, B, and C and the control apparatus 104 to communicate with each other, thereby causing the software of the control apparatus 104 to start control communication with each of the cassettes A, B, and C. This control communication allows the software of the control apparatus 104 to recognize that each of the radiographic imaging units 102a, 102b, and 102c is mounted on the platform 101, and also recognize a position where each of the cassettes A, B, and C is mounted on the holder. How the position recognition proceeds will be described below.

When the user completes the operation of mounting the radiographic imaging units 102a, 102b, and 102c, and the software can confirm that the radiographic imaging units 102a, 102b, and 102c are mounted normally, the software displays the completion of the preparation on the touch panel monitor 108 connected to the control apparatus 104. The user confirms the display indicating the completion of the preparation, and carries out the image-capturing. As illustrated in FIG. 1, the image-capturing is carried out in such a manner that a subject is positioned in front of the platform 101, and the subject in a wide range extending across the plurality of radiographic imaging units 102a, 102b, and 102c can be imaged by being irradiated with the radiation a single time.

After the image-capturing is carried out, a main control circuit 150 of each of the cassettes A, B, and C generates image data by scanning a two-dimensional image sensor 120. The generated image data is transferred to the control apparatus 104. In this case, the image data may be transferred with use of a communication path via a wired communication circuit 180 and the radiographic imaging unit connector 107 built in the radiographic imaging unit 102, the platform connector 206, and the like. Alternatively, the image data may be transferred via a wireless communication circuit 160 built in the radiographic imaging unit 102, and a not-illustrated wireless access point connected to the control apparatus 104.

The control apparatus 104 performs image processing for rearranging the images received from the individual radiographic imaging units 102a, 102b, and 102c by referring to recognized information about the positions where the cassettes A, B, and C are mounted, and connectively combines them. The combined image is presented to the user as a stitch imaging image that contains information of the subject in the wide range.

Figure 3:
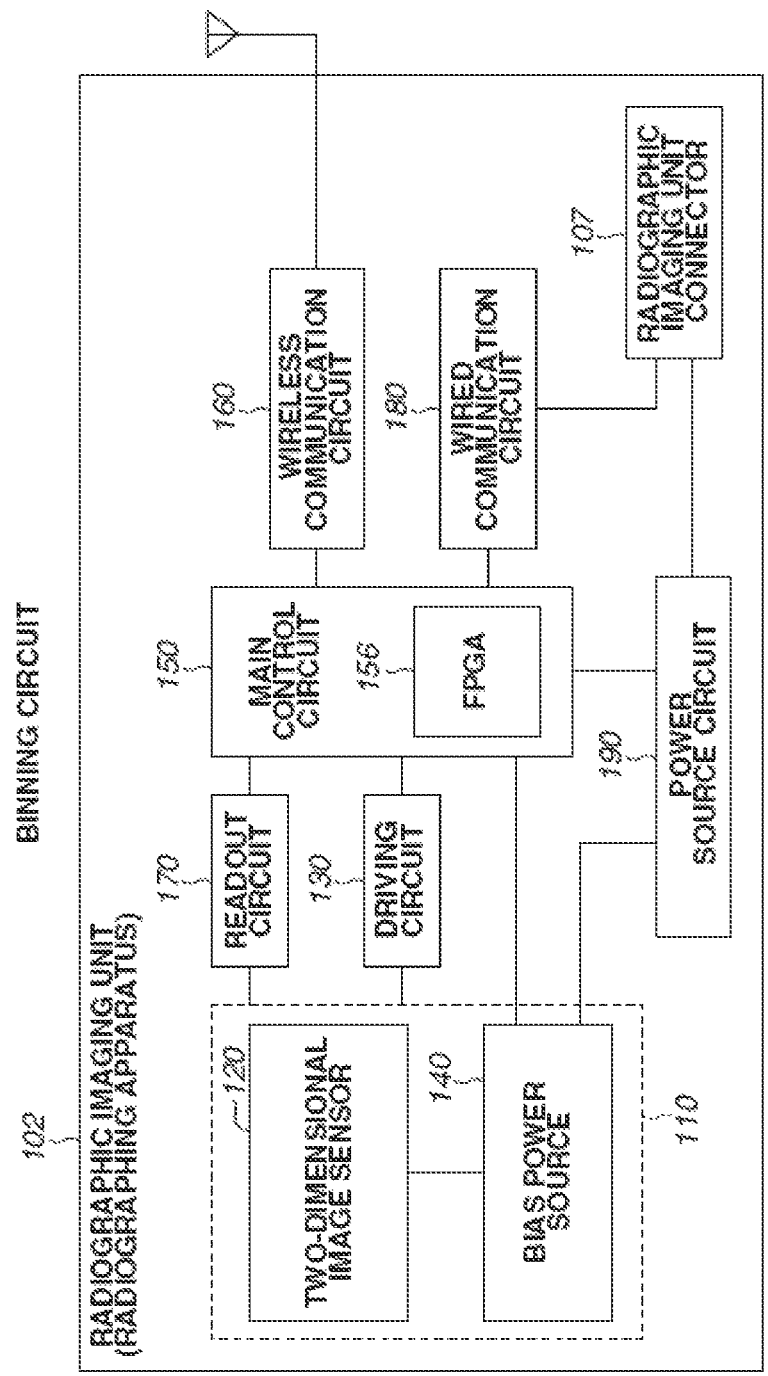
FIG. 3 is a block diagram illustrating a configuration of a radiographic imaging unit according to the exemplary embodiment.

A configuration of the radiographic imaging unit (a radiographing apparatus) 102 according to the present exemplary embodiment will be described with reference to FIG. 3. The radiographic imaging unit 102 includes a radiation sensor 110, a driving circuit 130, a readout circuit 170, the main control circuit 150, the wireless communication circuit 160, the wired communication circuit 180, the radiographic imaging unit connector 107, and a power source circuit 190. The radiation sensor 110 includes the two-dimensional image sensor 120. The two-dimensional image sensor 120 includes a pixel array in which a plurality of pixels is arrayed in the form of a matrix, a row selection line that is commonly connected to pixels lined up in a row direction and transmits a driving signal issued from the driving circuit 130, and a column signal line that is commonly connected to pixels lined up in a column direction and transmits an image signal to the readout circuit 170. A bias power source 140 is connected to each of the pixels of the two-dimensional image sensor 120. The pixels each include a photoelectric conversion element having one end connected to the bias power source 140, and a switching element connected to another end of this photoelectric conversion element. A base electrode of the switching element is connected to the row selection line, and the photoelectric conversion element and the column signal line are connected to a collector and an emitter of the switching element. The two-dimensional image sensor 120 generates the image based on a distribution of intensity of the radiation incident on this image sensor 120.

Other than those, the radiation sensor 110 may include a binning circuit that includes a switching element for connecting a plurality of pixels to one another, and combines image signals. For example, the switching element is connected to four pixels, vertically adjacent two pixels and horizontally adjacent two pixels. This configuration allows the radiation sensor 110 to combine the image signals before the image signals are digitized.

The driving circuit 130 controls an on state and an off state of the switching element by outputting the driving signal. When the switching element is controlled into the off state, this causes the image signal to be stored into a parasitic capacitance or the like of the photoelectric conversion element. When the switching element is controlled into the on state, this causes the stored image signal to be output via the column signal line. The readout circuit 170 includes an amplifier for amplifying the image signal output from the radiation sensor 110, and an analog-to-digital (A/D) converter for converting the image signal into a digital signal. The image signal is read out as the digital signal by them.

The driving circuit 130 performs control of collectively applying off-state voltages and control of sequentially applying on-state voltages to the row selection lines corresponding to the individual rows of the pixel array. The off-state voltages cause the radiation sensor 110 to transition to a storage state. The control of sequentially applying the on-state voltages causes the signals of the pixel array to be sequentially output to the readout circuit 170. By theses control procedures, the radiographic imaging unit 102 performs an operation of initializing the pixel array before causing the radiation sensor 110 to transition to the storage state, and an operation of reading out the image signals acquired from the storage.

The driving circuit 130 may conduct interlace driving of sequentially applying the on-state voltages to 2n rows, i.e., even-numbered rows, and then sequentially applying the on-state voltages to 2n−1 rows, i.e., odd-numbered rows after that. By this driving, the driving circuit 130 realizes reading out the image signals while thinning out the image signals. The thinning-out driving is not limited to the method that conducts this driving at intervals of one row as described above, and may be set to be conducted at intervals of two rows or m−1 rows. A desired value is adopted as a rate at which the image signals are thinned out in this manner. The driving circuit 130 may be set to sequentially apply the on-state voltages, like sequentially applying the on-state voltages to an mn row, an mn+1 row, an mn+2 row, . . . and an mn+(m−1) row, when m−1 is set as the rate at which the image signals are thinned out.

Alternatively, the driving circuit 130 can also conduct partial readout of the image signals, which means outputting image signals acquired from pixels around a center of the pixel array prior to the other image signals. In this case, supposing that the pixel array is constituted by M rows and N columns, M/2×N/2 image signals of an M/4+1 row to a 3M/4 row and an N/4+1 column to a 3N/4 column are output. The above-described operations performed by the driving circuit 130 are performed according to control from the main control circuit 150.

The main control circuit 150 integrally controls the radiographic imaging unit 102. Further, the main control circuit 150 includes a processing circuit implemented by a field-programmable gate array (FPGA) 156, and generates the radiographic image and performs the image processing thereby. The FPGA 156 can perform processing for acquiring an image small in data amount by, for example, the binning processing that sums up values of the adjacent 2×2 pixels, the thinning-out processing that partially thins out the pixels and partially extracts the pixels, or processing that extracts a continuous region, when acquiring the digital radiographic image.

Further, examples of the image processing that may be performed by the FPGA 156 include a dark correction for reducing a dark current component in the radiographic image, a gain correction for correcting a variation in an input/output characteristic of the pixel, a correction of a defective pixel, and processing for reducing a noise, such as a line noise.

The wireless communication circuit 160 and the wired communication circuit 180 can transmit and receive a control command and data, such as a signal from the control apparatus 104 and the radiation generation unit 100. Further, the wireless communication circuit 160 transmits a signal indicating a state of the radiographic imaging unit 102, and the radiographic image. The wireless communication circuit 160 includes an antenna, and performs wireless communication mainly when the wired cable 205 is not connected to the radiographic imaging unit connector 107. The radiographic imaging unit connector 107 is connected to the wired communication circuit 180, and the wired communication circuit 180 controls the wired communication. The connector 107 is provided for the communication and the power supply, and the communicated information and the power are transmitted to the wired communication circuit 180 and the power source circuit 190, respectively. The power source circuit 190 includes a battery, and produces a voltage required for the operation of the radiographic imaging unit 102 to supply the voltage to each of the units. The main control circuit 150 specifies which communication method should be used, the wireless communication or the wired communication. For example, the wired communication is specified if the wired cable 205 is connected to the connector 107, and the wireless communication is specified if the wired cable 205 is not connected but a connection via the wireless communication is established. Neither communication method is specified if the wired cable 205 is not connected and a connection via the wireless connection is also not established. In this case, for example, the radiographic image is not transmitted, and is stored into a nonvolatile memory connected to the main control circuit 150.

If transmitting the radiographic image with any of the communication methods specified, the main control circuit 150 transfers a preview image smaller in data amount than the radiographic image acquired by the radiation sensor 110 prior to this radiographic image. Then, the main control circuit 150 transmits an image that contains data uncontained in the preview image after completion of the transmission of this preview image.

This transmission allows the control apparatus 104 side to quickly check whether the image-capturing has been appropriate. The preview image and the image that contains the data uncontained in the preview image may be transmitted according to the readout of the image signals by the readout circuit 170 and the generation of the preview image by the main control circuit 150. Alternatively, the main control circuit 150 may be set to transmit these images according to a signal from the control apparatus 104. In this manner, the control apparatus 104 controls the communication with the plurality of radiographic imaging units 102a, 102b, and 102c, which can reduce an influence due to simultaneous transmission of large-volume data from the plurality of radiographic imaging units 102a, 102b, and 102c, thereby realizing efficient image communication.

Because this influence on the communication can be less likely to arise in some cases, for example, when the radiographic imaging unit 102 is connected to the control apparatus 104 via the wired communication or the communication capacity is sufficiently large, the main control circuit 150 may be configured to change the method for transmitting the images according to the communication method between the control apparatus 104 and the radiographic imaging unit 102.

One of states of the radiographic imaging unit 102 is a first state in which power is supplied only to the wireless communication circuit 160 and the wired communication circuit 180, and no power is supplied from the bias power source 140 to the two-dimensional image sensor 120 (a so-called sleep state). Further, another state of the radiographic imaging unit 102 is a second state in which power is supplied from the bias power source 140 to the two-dimensional image sensor 120. In the second state, the initialization operation is conclusively performed, and the radiographic imaging unit 102 is ready to generate the image by transitioning to the storage state in response to an instruction from outside. The radiographic imaging unit 102 transmits the signal indicating the above-described state according to a request signal from outside.

In a case where the radiation generation unit 100 is provided with the interface unit 203, synchronized communication is performed between the radiation generation unit 100 and the radiographic imaging unit 102. In response to pressing of the irradiation switch, the interface unit 203 transmits a first signal to each of the radiographic imaging units 102a, 102b, and 102c. According to this first signal, the driving circuit 130 of each of the radiographic imaging units 102a, 102b, and 102c causes the two-dimensional image sensor 120 to perform the initialization operation, and to transition to the storage state. Upon completion of the initialization and the transition to the storage state, each of the radiographic imaging units 102a, 102b, and 102c transmits a second signal to the interface unit 203. The interface unit 203 determines whether the second signals are received from all of radiographic imaging units 102 to be used for a certain stitch imaging, and inputs a signal for permitting the irradiation to the generation control unit 100b if the interface unit 203 has determined that the second signals are received from all of them. According thereto, the radiation is emitted from the radiation irradiation unit 100a for the irradiation. Controlling the units in this manner can prevent the radiation irradiation from being carried out before the radiographic imaging units 102a, 102b, and 102c transition to the storage state, thereby reducing unnecessary exposure.

In a case where the radiation generation unit 100 is not provided with the interface unit 203, the radiation generation unit 100 irradiates the subject with the radiation in response to the pressing of the irradiation switch. Each of the radiographic imaging units 102a, 102b, and 102c detects this start of the radiation irradiation, and transitions to the storage state. The radiographic imaging unit 102a, 102b, and 102c may each detect the start of the irradiation based on a signal acquired by the two-dimensional image sensor 120, or may detect the start of the irradiation by a sensor for detecting the start of the irradiation that is provided separately from the radiation sensor 110.

The main control circuit 150 specifies which mode should be employed, a first image-capturing mode of performing the synchronized communication or a second image-capturing mode of detecting the radiation, according to a signal input from outside.

Figure 4:
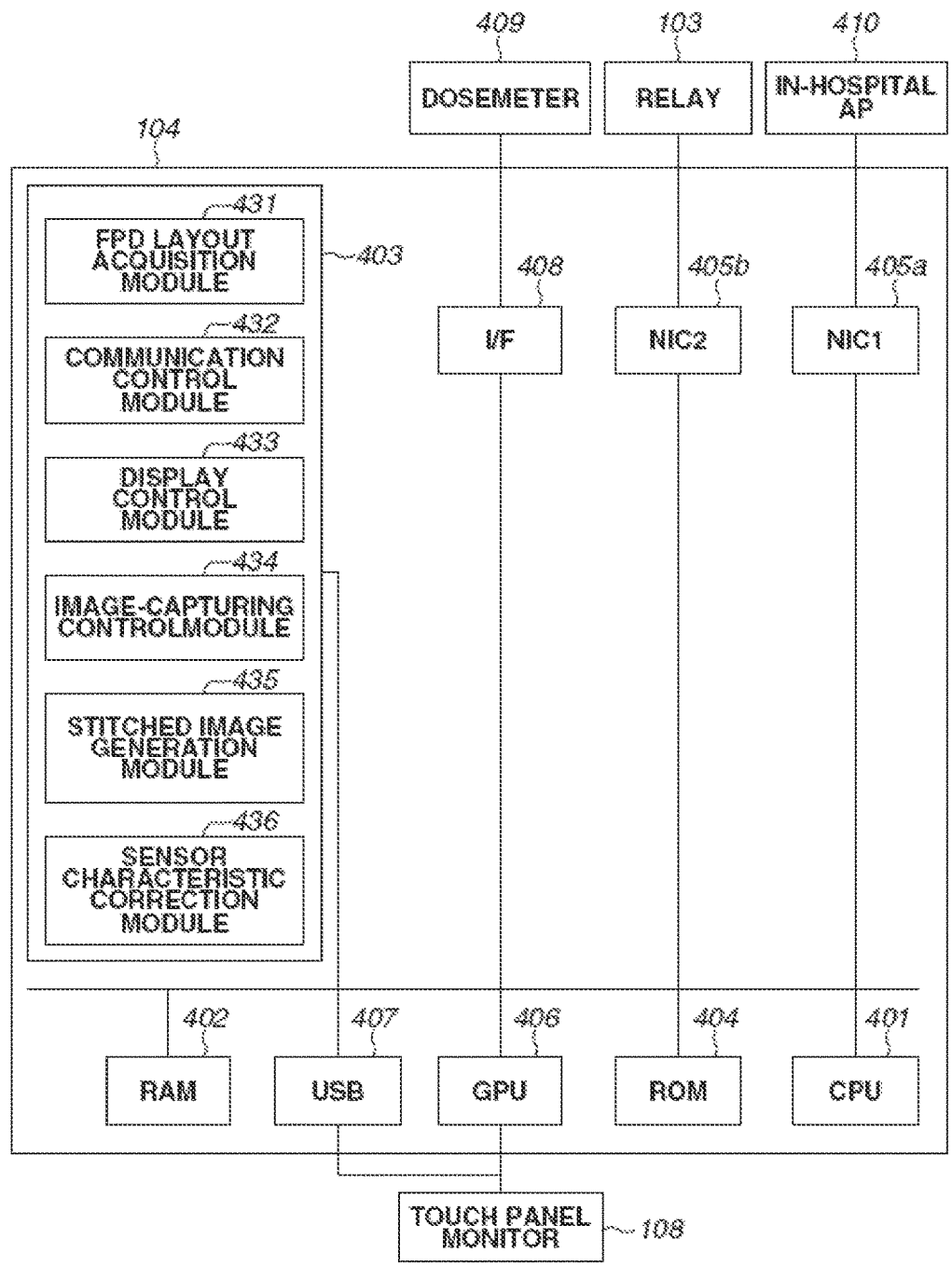
FIG. 4 is a block diagram illustrating a configuration of a control apparatus according to the exemplary embodiment.

A configuration of the control apparatus 104 according to the present exemplary embodiment will be described with reference to FIG. 4. The control apparatus 104 includes a central processing unit (CPU) 401, a random access memory (RAM) 402, a storage unit 403, a read only memory (ROM) 404, network interface cards (NICs) 405 (405a and 405b), a graphic processing unit (GPU) 406, a universal serial bus (USB) interface 407, and a communication interface (I/F) 408. These components are communicably connected to one another via an internal bus. The CPU 401 is a control circuit that comprehensively controls the control apparatus 104 and each of units connected to the control apparatus 104, and may include a plurality of CPUs. The RAM 402 is a memory used for loading a program for performing, for example, processing illustrated in FIG. 6 that will be described below, and various kinds of parameters, which are stored in the storage unit 403 or the like. The CPU 401 sequentially executes commands contained in the program loaded into this RAM 402, by which the processing according to the present exemplary embodiment is realized. The storage unit 403 is a memory such as a hard disk drive (HDD) and a solid state drive (SSD), and stores the above-described program, the radiographic image such as the stitched image acquired by the image-capturing, the image-capturing order, the image-capturing information, and in addition thereto, the various kinds of parameters. The NICs 405 are an example of a communication unit that communicates with an external apparatus. The control apparatus 104 according to the present exemplary embodiment includes a first NIC 405a and a second NIC 405b. The first NIC 405a is connected to an in-hospital access point (AP) 410 for connecting to an in-hospital network, and the second NIC 405b is connected to the relay 103 that relays the communication of the radiographing system. The GPU 406 is an image processing unit, and performs the image processing according to control from the CPU 401. An image acquired as a result of the image processing is output and displayed onto the touch panel monitor 108. The USB I/F 407 is a communication unit that acquires information relating to an operation input from the touch panel monitor 108, and is interpreted as the operation input by the CPU 401. The communication I/F 408 is, for example, a communication unit supporting a standard such as Recommended Standard 232 version C (RS232C), Ethernet (registered trademark), and USB, and communicates with a dosemeter (a dose measurement device) 409 to receive information indicating a radiation dose.

The program stored in the storage unit 403 includes, for example, a flat panel detector (FPD) (radiographic imaging unit) layout acquisition module 431, a communication control module 432, a display control module 433, an image-capturing control module 434, a stitched image generation module 435, and a sensor characteristic correction module 436.

The FPD layout acquisition module 431 acquires information indicating a layout relationship among the plurality of radiographic imaging units 102a, 102b, and 102c to be used to carry out the one stitch imaging. The information indicating the layout relationship is, for example, information indicating that the radiographic imaging units 102a, 102b, and 102c are laid out so as to be arranged in this order, or information indicating that the radiographic imaging unit 102b is located in the middle of them. The information indicating the layout relationship may contain information indicating rotational states of the radiographic imaging units 102a, 102b, and 102c. Such information indicating the layout relationship is acquired by the CPU 401 based on, for example, information, received by the second NIC 405b, indicating the communication paths of the radiographic imaging units 102a, 102b, and 102c, and correspondence information, stored in the storage unit 403, indicating correspondence relationships between the communication paths and the layout positions. For example, in a case where the platform connectors 206a, 206b, and 206c are disposed fixedly relative to the housing portions 201a, 201b, and 201c as illustrated in FIG. 2, the layout positions of the plurality of radiographic imaging units 102a, 102b, and 102c can be identified by referring to the information indicating the communication paths. For example, in a case where the relay 103 is a layer 2 network switch, the relay 103 performs an operation of learning relationships between the physical ports and media access control (MAC) addresses, and correspondence relationships between the radiographic imaging units 102a, 102b, and 102c and the physical ports are acquired as the information indicating the communication paths with use of this operation.

This information indicating the layout relationships acquired in this manner is stored into the storage unit 403. Alternatively, the second NIC 405b may receive the information indicating the layout relationship. In this case, the relay 103 or the platform 101 is assumed to have a function of acquiring the information indicating the layout relationship based on the information indicating the communication paths and the like.

The information indicating the layout relationship is, for example, referred to during the course of execution of the stitched image generation module 435, and used in the processing for stitching the plurality of radiographic images. The information indicating the layout relationship in this case is information for identifying which radiographic images contain an overlap region therebetween. Further, the information indicating the layout relationship is, for example, referred to by the CPU 401 to determine which radiographic image should be subjected to execution of the correction processing for removing the structure appearing therein during the course of execution of the correction module 436. The information indicating the layout relationship in this case is information for identifying which one of the radiographic imaging units 102a, 102b, and 102c has output the image with the structure appearing therein, and corresponds to information for identifying which one of the radiographic imaging units 102a, 102b, and 102c radiographic imaging unit is located in the middle of the radiographic imaging units 102a, 102b, and 102c in the imaging system illustrated in FIG. 1.

The communication control module 432 controls the communication by the first NIC 405a and the second NIC 405b. Execution of the communication control module 432 causes, for example, the control apparatus 104 to transmit the signals for causing the states of the plurality of radiographic imaging units 102a, 102b, and 102c to transition to the second state to the radiographic imaging units 102a, 102b, and 102c according to an operation input from the touch panel monitor 108 or the like. This operation input is carried out, for example, according to an operation input for selecting one of a plurality of image-capturing conditions contained in the image-capturing order and then the CPU 401 specifying this image-capturing condition based thereon. In response to this operation input, the second NIC 405b transmits the signals for causing the states to transition, to the radiographic imaging units 102a, 102b, and 102c. Then, the second NIC 405b will receive response signals thereto.

Further, the execution of the communication control module 432 causes, for example, the control apparatus 104 to receive the radiographic image from each of the plurality of radiographic imaging units 102a, 102b, and 102c. At this time, the control apparatus 104 is assumed to first receive the preview image (a first image) small in data amount and then receive the image that contains the remaining data (a second image) after that, from each of the plurality of radiographic imaging units 102a, 102b, and 102c. In this case, the control apparatus 104 is assumed to, when receiving the preview image (the first image) from one radiographic imaging unit 102, restrict the reception of the first or second image from the other radiographic imaging units 102. Therefore, each of the radiographic imaging units 102a, 102b, and 102c is assumed to be set to transmit the image according to an instruction from the control apparatus 104, and the control apparatus 104 is assumed to instruct one radiographic imaging unit 102 to transmit the second image according to, for example, completion of the reception of the preview images (the first images) from all of the radiographic imaging units 102a, 102b, and 102c. By this control, the large-volume data is prevented from being transmitted from the plurality of radiographic imaging units 102a, 102b, and 102c to the relay 103 simultaneously, thereby improving efficiency of the communication.

The radiographic imaging unit side can also perform a transmission method in which the radiographic image is transmitted in response to the readout of the image signals (a first transmission method), besides the transmission method in which the image is transmitted in response to the instruction signal as described above (a second transmission method). The transmission method to be performed is, for example, specified according to a signal from the control apparatus 104. For example, the first transmission method is specified in the case where the radiographic imaging unit 102 performs the wireless communication, and the second transmission method is specified in the case where the radiographic imaging unit 102 performs the wired communication. In the case where the transmission method is specified according to the communication configuration in this manner, the radiographic imaging unit 102 can specify the transmission method regardless of the signal from outside.

Besides that, by executing the communication control module 432, the CPU 401 cause a DICOM image file containing the radiographic image acquired by the radiographic imaging or the stitch imaging to be transmitted to the PACS 153 via the first NIC 405a.

In one exemplary embodiment, the FPGA 156 of the radiographic imaging unit 102 performs the processing for correcting the structure appearing in the radiographic image. In this case, the CPU 401 specifies the radiographic imaging unit 102 to be instructed to perform the processing for correcting the structure among the plurality of radiographic imaging units 102a, 102b, and 102c during the course of the execution of the communication control module 432. As an example thereof, the radiographic imaging unit 102b located in the middle of the radiographic imaging units 102a, 102b, and 102c illustrated in FIG. 1 is specified with use of the information indicating the layout relationship. Then, the CPU 401 causes the second NIC 405b to transmit an instruction signal for instructing the radiographic imaging unit 102b to perform the processing for correcting the structure to the radiographic imaging unit 102b.

The display control module 433 is used in processing for controlling a content of a display screen displayed on the touch panel monitor 108. This processing is, for example, processing for displaying the image-capturing condition corresponding to the stitch imaging and processing for displaying the generated stitched image on the display screen. Further, by this module, the CPU 401 determines whether any one of the above-described plurality of radiographic imaging units 102a, 102b, and 102c is in the first state or all of the above-described plurality of radiographic imaging units 102a, 102b, and 102c are in the second state based on the information indicating the respective states of the plurality of radiographic imaging units 102a, 102b, and 102c. Then, the CPU 401 controls the display of the touch panel monitor 108 according to this determination. The second NIC 405b receives the state information indicating whether the radiographic imaging unit 102 is in the first state, which is not a state prepared for the acquisition of the radiographic image, or the second state, which is the state prepared for the acquisition of the radiographic image, with respect to each of the plurality of radiographic imaging units 102a, 102b, and 102c. The CPU 401 determines whether any one of the above-described plurality of radiographic imaging units 102a, 102b, and 102c is in the first state or all of the above-described plurality of radiographic imaging units 102a, 102b, and 102c are in the second state.

Controlling the display in this manner allows the control apparatus 140 to present a display indicating whether all of the radiographic imaging units 102a, 102b, and 102c are in the state capable of the image-capturing, instead of a display individually indicating the state of each of the radiographic imaging units 102a, 102b, and 102c, thereby allowing the user to intuitively recognize whether the stitch imaging can be carried out. Alternatively, the control apparatus 104 may also be configured to present the display individually indicating the state of each of the radiographic imaging units 102a, 102b, and 102c, together with the display indicating whether all of the radiographic imaging units 102a, 102b, and 102c are in the state capable of the image-capturing, and it is apparent that such a display allows the user to readily take some measures, for example, when one radiographic imaging unit 102 cannot carry out the image-capturing due to an error.

The image-capturing control module 434 is a program for causing the CPU 401 to integrally control the execution of the radiographic imaging including the stitch imaging. By the image-capturing control module 434, for example, the CPU 401 specifies the image-capturing condition according to the operation input, transmits the signal for requesting the state of each of the units of the radiographic imaging unit 102, and controls the reception of the radiographic images.

The stitched image generation module 435 generates the stitched image from the plurality of radiographic images with use of the CPU 401 and the GPU 406. The stitched image is generated by positioning processing for defining a positional relationship among the plurality of radiographic images. The positioning processing includes rough adjustment processing for determining a rough layout among the images, and fine adjustment processing for adjusting the positions among the images with precision of several pixels, or precision of one pixel or less.

The rough adjustment processing is processing for determining which ends correspond to each other among the ends of the individual radiographic images with use of the information indicating the layout relationship among the plurality of radiographic imaging units 102a, 102b, and 102c. This processing is performed with use of the layout information acquired from the processing performed by the FPD layout acquisition module 431. The fine adjustment processing is performed by, for example, pattern matching processing with use of image information of a region overlapping among the plurality of radiographic images. This processing may be performed after the processing by the correction module 436.

The correction module 436 performs the processing for correcting an influence due to the characteristic of the sensor and the correction processing for reducing the number of structures appearing in the radiographic image(s) with use of the CPU 401 and the GPU 406. The processing for correcting the characteristic of the sensor includes, for example, the processing for correcting influences of the variation in the input/output characteristic of each of the pixels, the defective pixel, and the like, and this processing is performed with use of data such as data for the gain correction and a defective map that are acquired in advance. The correction processing for reducing the number of structures appearing in the radiographic image(s) is performed with use of the correction data for reducing the number of structures. This correction data is acquired by subtracting data acquired by carrying out the image-capturing with use of the same imaging system as the imaging system that captures this radiographic image and without the presence of the subject, after dividing this data by the data for the gain correction or dividing this data thereby after logarithmically converting this data. This correction data may be stored in the radiographic imaging unit 102 in advance at the time of shipment from a factory or the like, or may be acquired before the stitch imaging is carried out in each hospital.

In another exemplary embodiment, the function of the relay 103 is assumed to be provided to the control apparatus 104. In this case, the stitch imaging system is configured in such a manner that, for example, the control apparatus 104 includes three second NICs 405b that communicate with the radiographic imaging units 102a, 102b, and 102c, and cables connected to the radiographic imaging units 102a, 102b, and 102c are directly connected to the control apparatus 104.

The display screen according to the present exemplary embodiment will be described with reference to FIG. 5. A display screen 500 includes an image area 501 where the radiographic image is displayed, a subject area 502 where information about the subject is displayed, a image-capturing information area 503 where the image-capturing information is displayed, an end button 504, and a state area 507 where information indicating the states of the plurality of radiographic imaging units 102a, 102b, and 102c is displayed. The example illustrated in FIG. 5 indicates the display screen after the stitch imaging has been already carried out once when the stitch imaging is supposed to be carried out a plurality of times. A stitched image 508 is displayed in the image area 501. Information about a subject A is displayed in the subject area 502. Image-capturing information 505a about the image-capturing site that is the entire lower limb, and image-capturing information 505b about the image-capturing site that is the entire spine are displayed in the image-capturing information area 503 as image-capturing information 505. The information about the image-capturing site, and the number of radiographic imaging units 102 used or to be used for the stitch imaging thereof are displayed side by side as the image-capturing information 505. The image-capturing information 505a is image-capturing information about the image-capturing that has been already carried out, and thumbnails of the radiographic images from the plurality of radiographic imaging units 102 are displayed therein while being arranged in a layout according to the layout relationship among the radiographic imaging units 102. In the example illustrated in FIG. 5, a thumbnail 506b of the radiographic image from the radiographic imaging unit 102b, a thumbnail 506c of the radiographic image from the radiographic imaging unit 102c, and a thumbnail 506a of the radiographic image from the radiographic imaging unit 102a are displayed while being arranged in this order. In this manner, the thumbnails are arranged based on the layout information, which allows the user to easily check whether the stitch imaging has been appropriately carried out. On the other hand, if there is an error in the layout information, this results in a failure to arrange the thumbnails appropriately, which allows the user to be notified of whether the layout information is appropriate in an easily understandable manner.

On the other hand, the image-capturing information 505b is image-capturing information about the image-capturing that is not yet carried out, and a display indicating the layout relationship among the plurality of radiographic imaging units 102 is presented therein instead of the thumbnails. In the example illustrated in FIG. 5, a display ("FPD B") 507b corresponding to the radiographic imaging unit 102b, a display ("FPD C") 507c corresponding to the radiographic imaging unit 102c, and a display ("FPD A") 507a corresponding to the radiographic imaging unit 102a are displayed while being arranged so as to be located at display positions according to the layout relationship among the radiographic imaging units 102a, 102b, and 102c. This display allows the user to check whether the radiographic imaging units 102a, 102b, and 102c are appropriately laid out on the touch panel monitor 108 of the control apparatus 104 before the image-capturing. The control apparatus 104 may be configured to cause the states of the radiographic imaging units 102a, 102b, and 102c to be displayed by the displays 507a, 507b, and 507c at this time.

The information indicating the states of the plurality of radiographic imaging units 102 is displayed in the state area 507. The radiographic imaging units 102 for which the information indicating the states is displayed there may be the radiographic imaging units 102 corresponding to the currently specified image-capturing condition. If the image-capturing condition corresponding to the stitch imaging is specified as illustrated in FIG. 5, the information indicating the states of the radiographic imaging units 102a, 102b, and 102c is displayed therein. In the state area 507, the pieces of information indicating the states of the plurality of radiographic imaging units 102 are displayed while being arranged on the display screen 500 at display positions according to the layout state among this plurality of radiographic imaging units 102. For example, if the radiographic imaging unit 102b and the radiographic imaging unit 102c are interchanged with the display screen displayed as illustrated in FIG. 5, this interchange results in a display of the respective states of the radiographic imaging units 102c, 102b, and 102a arranged in this order in the state area 507. Presenting the display in this manner allows the user to easily check the layout relationship among the plurality of radiographic imaging units 102.

The end button 504 is a button for ending an examination regarding the plurality of pieces of image-capturing information displayed on the display screen 500. If the end button 504 is pressed after an end of the image-capturing operations corresponding to all pieces of image-capturing information contained in this examination, this examination is ended. In this case, the CPU 401 generates the DICOM image file of the radiographic images regarding this examination, and causes the first NIC 405a to transmit this file to the PACS 154. On the other hand, if the end button 504 is pressed before the end of the image-capturing operations corresponding to the pieces of image-capturing information contained in this examination, this examination is set into a suspended state, and is stored into the storage unit 403 together with flag information indicating the suspended state.

The control apparatus 104 may be configured to cause the states of the individual radiographic imaging units 102 to be displayed in the displays 507a, 507b, and 507c, and cause readiness or unreadiness for the image-capturing to be clearly displayed in the state area 507 as a display indicating whether the stitch imaging can be carried out. In this case, the state area 507 is displayed in such a manner that a color of the state area 507 is, for example, grayed if even any one of the plurality of radiographic imaging units 102 is in the first state, i.e., is not in the state prepared for the acquisition of the radiographic image. Further, for example, a text "NOT READY" is displayed in addition thereto. The prohibition of the stitch imaging is clearly indicated by this display. On the other hand, if all of the plurality of radiographic imaging units 102 are in the second state prepared for the acquisition of the radiographic image, the color of the state area 507 is, for example, greened, and a text "READY" is displayed in addition thereto. The permission of the stitch imaging is clearly indicated by this display. In this manner, the display of the touch panel monitor 108 is controlled according to whether any one of the plurality of radiographic imaging units 102 is in the first state or all of the plurality of radiographic imaging units 102 are in the second state, by which the readiness or the unreadiness for the image-capturing is clearly indicated.

Figure 6:
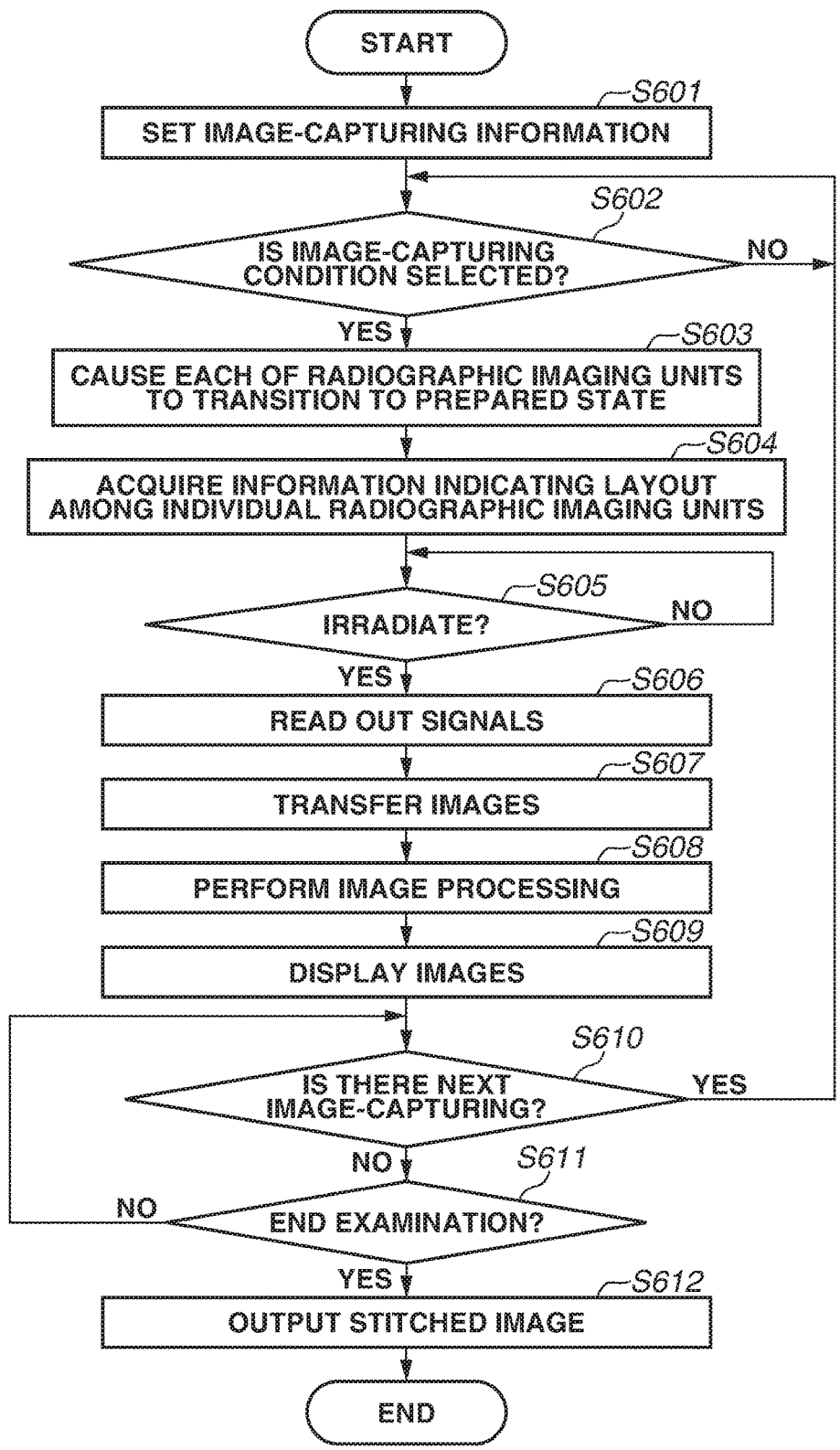
FIG. 6 is a flowchart illustrating a flow of processing regarding stitch imaging according to the exemplary embodiment.

A flow of processing regarding the stitch imaging according to the present exemplary embodiment will be described with reference to a flowchart illustrated in FIG. 6. A processing entity that performs the following processing is the CPU 401 of the control apparatus 104, unless otherwise noted specifically. The flow of the processing from steps S601 to S612 is controlled by the image-capturing control module 434.

In step S601, the CPU 401 sets one of pieces of image-capturing information (pieces of examination information) input from the RIS 151 as an examination target. In this process, for example, according to an operation input by which the user selects one of the plurality of pieces of examination information displayed in the form of a list, the CPU 401 sets this image-capturing information (the examination information) as the image-capturing target. At this time, for example, the CPU 401 executes the display control module 433 to cause the display screen 500 to be displayed on the display unit.

In step S602, the CPU 401 determines whether an operation input for selecting the image-capturing condition corresponding to the stitch imaging that is contained in the image-capturing information (the examination information) is entered. At this time, if the image-capturing information (the examination information) contains a plurality of image-capturing conditions, information corresponding to the plurality of image-capturing conditions is displayed in the image-capturing information area 503 on the display screen 500, and the CPU 401 determines whether an operation input for selecting one of them is entered by the user. If the operation input for the selection is not entered (NO in step S602), the determination process in step S602 is repeated. If the operation input for the selection is entered (YES in step S602), the processing proceeds to a next process. The processing may be configured to automatically proceed to step S603 regardless of the process of step S602, if the image-capturing information (the examination information) contains only the image-capturing condition corresponding to the image-capturing (1).

In step S603, the CPU 401 specifies the image-capturing condition corresponding to the stitch imaging that has been selected by the operation input. Then, according to this specifying, the CPU 401 causes the second NIC 405b to transmit the signals for causing the states to transition to the prepared state to the plurality of radiographic imaging units 102a, 102b, and 102c involved in this stitch imaging. In response thereto, each of the radiographic imaging units 102a, 102b, and 102c apply the bias voltage to the two-dimensional image sensor 120 by the main control circuit 150 controlling the bias power source 140, if the bias voltage is not applied to the two-dimensional image sensor 120. After that, each of the radiographic imaging units 102a, 102b, and 102c carries out the initialization of reading out the image signals from the pixel array by the driving circuit 130 to read out dark current signals stored in the pixels. After an end of the initialization, each of the radiographic imaging units 102a, 102b, and 102c transmits, to the control apparatus 104, the state information indicating that each of the plurality of radiographic imaging units 102a, 102b, and 102c is in the second state, which is the state prepared for the acquisition of the radiographic image, after the completion of the initialization.

In step S604, the CPU 401 acquires the layout information indicating the layout relationship among the plurality of radiographic imaging units 102a, 102b, and 102c to be used for the stitch imaging. For example, in the case where the present processing is performed assuming that the stitch imaging system is a system such as the system illustrated in FIG. 1, the CPU 401 acquires the information indicating the respective communication paths of the plurality of radiographic imaging units 102a, 102b, and 102c from the relay 103. The relay 103 includes a plurality of physical ports to which the cables 205a, 205b, and 205c from the platform connectors 206a, 206b, and 206c respectively provided to the housing portions 201a, 201b, and 201c are connected. This relay 103 identifies which physical port each of the signals from the radiographic imaging units 102a, 102b, and 102c is input from, thereby generating the correspondence relationships between the physical ports and the radiographic imaging units 102a, 102b, and 102c, i.e., the information indicating the respective communication paths of the radiographic imaging units 102a, 102b, and 102c. The CPU 401 of the control apparatus 104 receives this information from the second NIC 405b. The CPU 401 acquires the information indicating the layout relationship from the information indicating the communication paths acquired in this manner.

Figure 5:
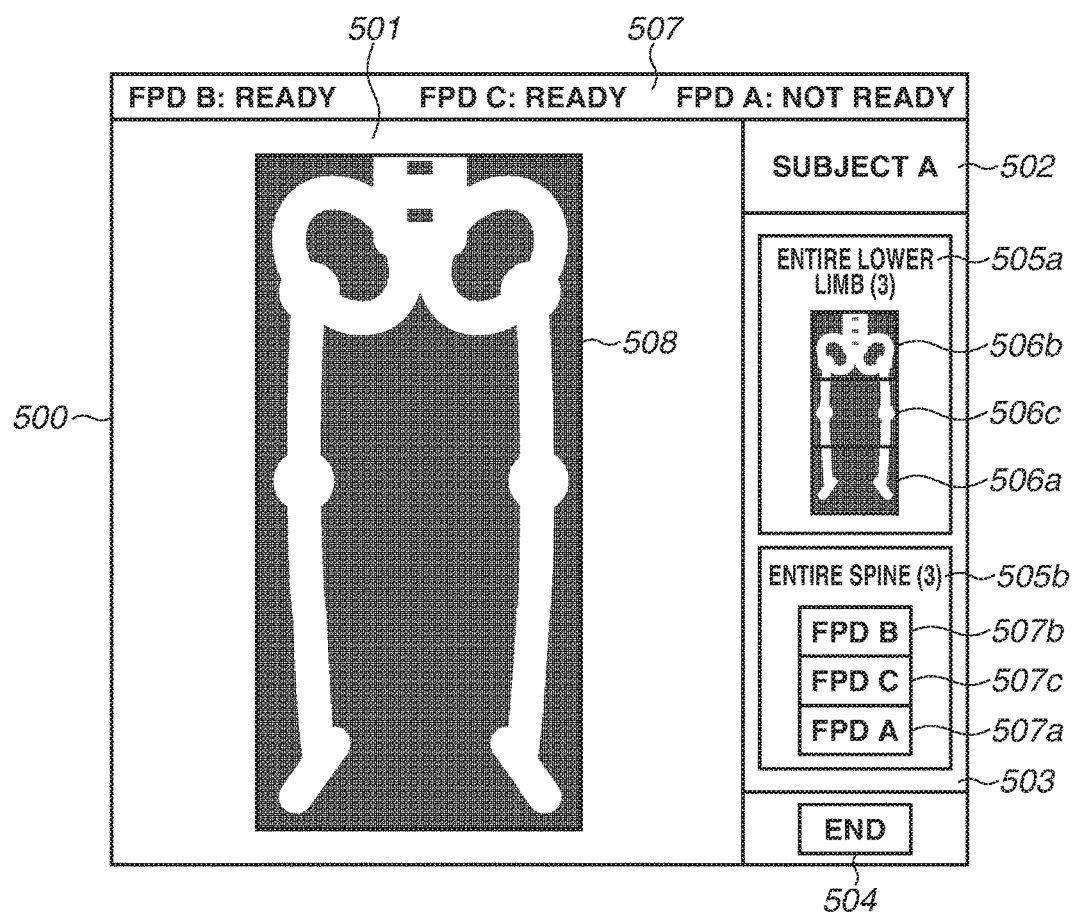
FIG. 5 illustrates an example of a display screen according to the exemplary embodiment.

As indicated by the image-capturing information 505b on the display screen 500 illustrated in FIG. 5, this information indicating the layout relationship is displayed as the information indicating the layout relationship among the plurality of radiographic imaging units 102a, 102b, and 102c to be used for the stitch imaging corresponding to this image-capturing information 505b.

In step S605, the CPU 401 determines whether the irradiation switch is pressed. If the irradiation switch is pressed (YES in step S605), the processing proceeds to step S606.

Whether the irradiation switch should be pressed is determined, for example, with use of the display based on the states of the plurality of radiographic imaging units 102a, 102b, and 102c displayed on the display screen 500. More specifically, the display of the specific area on the display screen 500 is controlled according to whether any one of the plurality of radiographic imaging units 102a, 102b, and 102c is in the first state or all of the plurality of radiographic imaging units 102a, 102b, and 102c are in the second state based on the state information acquired from each of the plurality of radiographic imaging units 102a, 102b, and 102c. This is as described in the description of the display screen 500 illustrated in FIG. 5.

In step S606, the driving circuit 130 of each of the radiographic imaging units 102a, 102b, and 102c reads out the image signals acquired by detecting the radiation with which the subject is irradiated by the readout circuit 170 to generate the digital radiographic image.

In step S607, the wired communication circuit 180 or the wireless communication circuit 160 of each of the radiographic imaging units 102a, 102b, and 102c transmits the generated digital radiographic image to the control apparatus 104. Each of the plurality of radiographic imaging units 102a, 102b, and 102c transmits the preview image small in data quantity and then transmits the image that contains the remaining data after that, thereby completing the transmission of the radiographic image acquired from the image-capturing. At this time, in a case where each of the radiographic imaging units 102a, 102b, and 102c transmits the radiographic image via the wired communication circuit 180, each of the radiographic imaging units 102a, 102b, and 102c employs the communication method that sequentially transmits the preview image and the image containing the remaining data in response to the readout of the image signals. This transmission is carried out asynchronously with the other radiographic imaging units 102. On the other hand, in a case where each of the radiographic imaging units 102a, 102b, and 102c transmits the images via the wireless communication circuit 160, each of the radiographic imaging units 102a, 102b, and 102c restricts the transmission of the image that contains the remaining data until the completion of the transmission of the preview images from all of the radiographic imaging units 102a, 102b, and 102c, in consideration of such a problem that this image transmission may weigh on the communication capacity.

In step S608, the CPU 401 of the control apparatus 104 performs the image processing on the plurality of radiographic images acquired from the plurality of radiographic imaging units 102a, 102b, and 102c with use of the GPU 406 and the like. This processing is, for example, the processing for generating the stitched image with use of the stitched image generation module 435, and the processing for reducing the number of structure images with use of the correction module 436. In the process of step S608, first, the CPU 401 performs the processing for acquiring a preview stitched image from the plurality of preview images, and then performs the processing for acquiring the stitched image from the plurality of radiographic images larger in data amount than these preview images after that. This processing is performed with use of the layout information acquired in step S604. The processing for reducing the number of structure images is performed on the radiographic image specified based on the layout information with use of the correction data prepared for the processing for reducing the number of structure images that is specified based on the layout information.

In step S609, the CPU 401 causes the preview stitched image and the stitched image acquired from the processing performed by the GPU 406 and the like to be displayed on the display unit.

In step S610, the CPU 401 determines whether there is an image-capturing condition on which the image-capturing is not yet carried out. If there is such an image-capturing condition (YES in step S610), the processing proceeds to step S602. Then, the CPU 401 performs the stitch imaging based on the new image-capturing condition. If there is no image-capturing condition on which the image-capturing is not yet carried out (NO in step S610), then in step S611, the CPU 401 determines whether to end the examination. If the CPU 401 does not end the examination (NO in step S611), the CPU 401 performs processing for waiting for an addition of an image-capturing condition on which the image-capturing is not yet carried out, or an instruction to end the examination. If the examination end button 504 is pressed at this time (YES in step S611), the CPU 401 ends the examination. In step S612, the CPU 401 causes the first NIC 405a to output the DICOM image file of the stitched image to the PACS 155. With this output, the examination that contains the stitch imaging is ended.

In the above-described example, the stitch imaging system is assumed to carry out the stitch imaging a plurality of times during a single examination. However, it is not limited thereto, and it may be assumed to carry out the stitch imaging together with image-capturing using a different image-capturing method from the stitch imaging during a single examination. In this manner, in the case of the imaging system capable of carrying out the stitch imaging, when carrying out the stitch imaging, the control apparatus 104 transmits the signals for causing the states of the plurality of radiographic imaging units 102a, 102b, and 102c to transition according to the specifying of the image-capturing condition. On the other hand, when carrying out the image-capturing using the single radiographic imaging unit 102, such as normal image-capturing, the control apparatus 104 transmits the signal for causing the state of this single radiographic imaging unit 102 to transition according to the specifying of the image-capturing condition. Further, when carrying out the stitch imaging, the control apparatus 104 controls the display based on the state information acquired from each of the plurality of radiographic imaging units 102a, 102b, and 102c according to whether any one of the plurality of radiographic imaging units 102a, 102b, and 102c is in the first state or all of the plurality of radiographic imaging units 102a, 102b, and 102c are in the second state. When carrying out the image-capturing using the single radiographic imaging unit 102, the control apparatus 104 causes the information indicating the state of this single radiographic imaging unit 102 to be displayed.

Further, when carrying out the stitch imaging, the control apparatus 104 acquires the layout information indicating the layout relationship among the plurality of radiographic imaging units 102a, 102b, and 102c. The radiographic image(s) acquired from at least one of the radiographic imaging unit(s) 102 specified based on this layout information is or are corrected based on the correction data specified based on the layout information.

Further, at the time executing the stitch imaging, the control is performed so as to restrict the transmission of the image according to the communication of the other radiographic imaging units 102 in consideration of the problem that the image transmission may weigh on the communication capacity. On the other hand, at the time of the image-capturing using the single radiographic imaging unit 102, the image that contains the remaining data is transmitted according to the end of the transmission of the preview image because priority is placed on transmitting the image as quickly as possible in this case.

Figure 7:
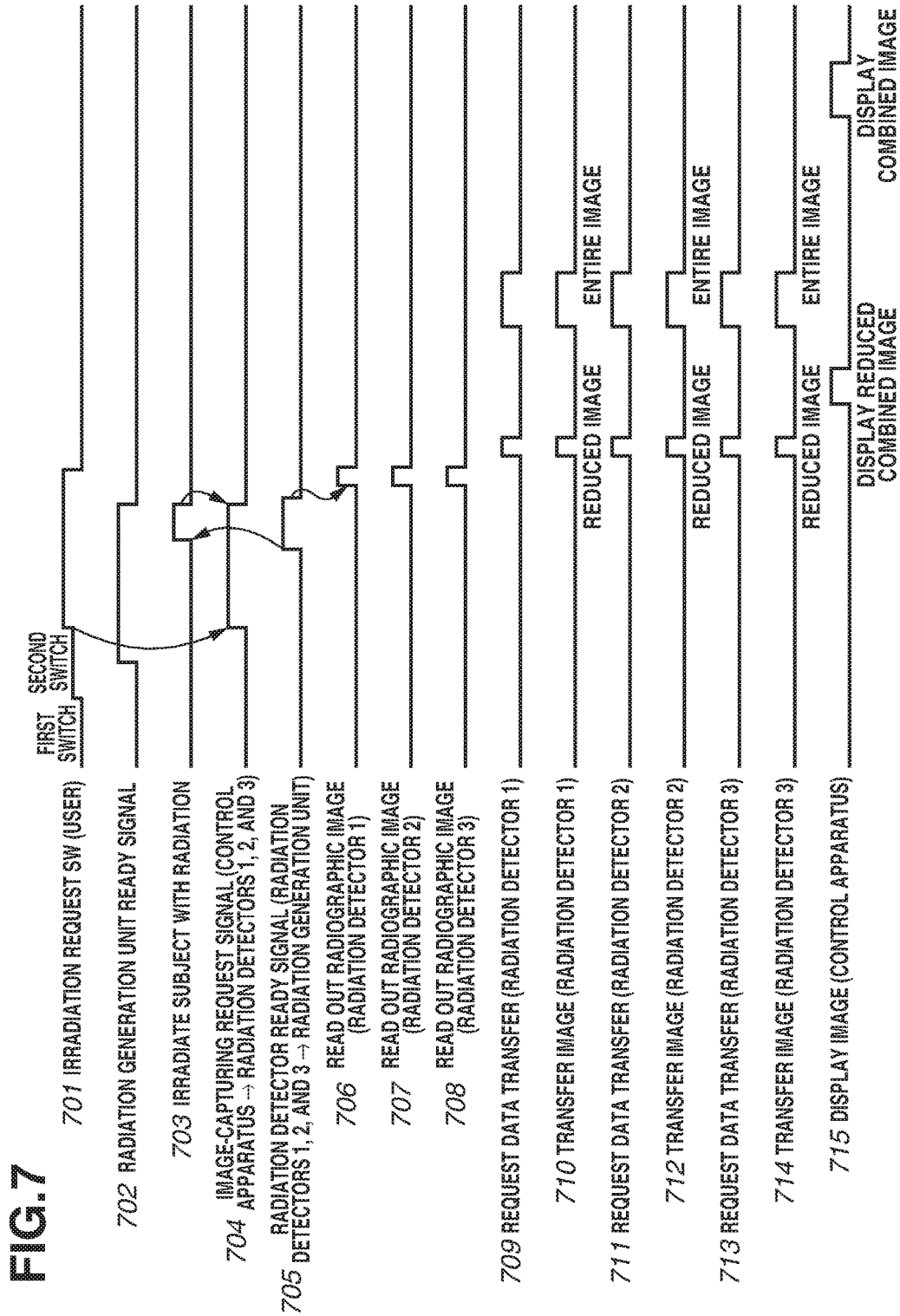
FIG. 7 is a timing chart illustrating a flow of photographing processing and processing for transferring images according to the exemplary embodiment.

Next, a flow of the processing for receiving the radiographic images from the plurality of radiographic imaging units 102a, 102b, and 102c (the radiographic imaging units 102a, 102b, and 102c (radiation detectors 1 to 3)), and the processing for displaying the stitched image will be described with reference to FIGS. 7 to 9. FIG. 7 is a timing chart illustrating an operation from the irradiation to the display of the combined image. In FIG. 7, a signal 701 indicates whether the irradiation switch is pressed by the user's operation. This irradiation switch includes a first switch and a second switch, and is configured to permit the second switch to be pressed when the first switch is in a pressed state. A generation unit READY signal 702 indicates that the radiation generation unit 100 is already prepared. A signal 703 indicates whether the subject is irradiated with the radiation. A signal 704 indicates an image-capturing request signal that is transmitted from the control apparatus 104 to each of the radiographic imaging units 102a, 102b, and 102c (the radiation detectors 1 to 3) based on the user's instruction. A radiographic imaging unit READY signal 705 indicates that all of the radiographic imaging units 102a, 102b, and 102c (the radiation detectors 1 to 3) have completed the preparation for the image-capturing. Signals 706, 707, and 708 indicate whether the images are read out at the radiographic imaging units 102a, 102b, and 102c (the radiation detectors 1 to 3), respectively. Signals 709, 711, and 713 indicate signals for requesting the data transfers to the radiographic imaging units 102a, 102b, and 102c, respectively. Timings 710, 712, and 714 indicate timings at which the radiographic imaging units 102a, 102b, and 102c transfer the images, respectively. A timing 715 indicates a timing at which the control apparatus 104 displays the images.

The radiation generation unit 100 starts preparation for the irradiation in response to pressing of the first switch of the irradiation switch, and the generation unit READY signal 702 rises upon completion of the preparation. Further, when the second switch is pressed with the first switch pressed, the radiation generation unit 100 causes the interface unit 203 to transmit the image-capturing request signal to each of the plurality of radiographic imaging units 102a, 102b, and 102c in response thereto. Each of the radiographic imaging units 102a, 102b, and 102c performs the initialization processing and transitions to the storage state in response thereto. As a result, each of the radiographic imaging units 102a, 102b, and 102c becomes ready to detect the radiographic image signals. Further, each of the radiographic imaging units 102a, 102b, and 102c transmits the radiographic imaging unit (detector) READY signal 705 to the radiation generation unit 100 in response thereto. The radiation is generated so as to be prevented from exceeding a preset irradiation time period while this radiographic imaging unit (detector) READY signal 705 is received, the generation unit (generator) READY signal 702 rises, and the second switch of the irradiation switch is in a pressed state.

During this irradiation time period, each of the radiographic imaging units 102a, 102b, and 102c is kept in the storage state, and detects the radiation to acquire the image signals. These image signals (the radiographic image signals) each contain a signal component acquired from the detection of the radiation and a dark component generated by the photoelectric conversion element. Each of the radiographic imaging units 102a, 102b, and 102c reads out these image signals from the pixel array, and acquires the digital radiographic image by the readout circuit 170. The readout signals 706, 707, and 708 may rise upon an elapse of a predetermined storage time period, or may rise, for example, in response to a signal indicating an end of the irradiation with the radiation from the radiation generation unit 100. With the above-described processing, each of the radiographic imaging units 102a, 102b, and 102c completes the processing for capturing the radiographic image. After that, each of the radiographic imaging units 102a, 102b, and 102c performs the processing for transferring this radiographic image.

The main control circuit 150 of each of the radiographic imaging units 102a, 102b, and 102c generates the preview image (a reduced image) small in data amount from the radiographic image by the thinning-out processing, addition processing, or the like. In parallel with this generation processing, the wired communication circuit 180 or the wireless communication circuit 160 transmits this preview image to the control apparatus 104.

The main control circuit 150 according to one exemplary embodiment causes transmission of the radiographic image (an entire image) based on which the preview image is generated after the transmission processing is completed with the transmission of the reduced image and reception of an acknowledgment (ACK) signal from the control apparatus 104. Especially in a case where the addition processing or other image processing is performed when the preview image is generated, and the original image cannot be reconstructed from the preview image, it is desirable to transmit the entire image.

Until reception of a specific signal from outside after the transmission of the preview image (the reduced image), the main control circuit 150 restricts the transmission of the image that contains data other than this preview image (e.g., the entire image). For example, the main control circuit 150 restricts the start of the transmission until the reception of this specific signal. The control apparatus 104 transmits this specific signal to each of the radiographic imaging units 102a, 102b, and 102c upon, for example, completion of the transmission of the preview image from each of the radiographic imaging units 102a, 102b, and 102c. This transmission of the specific signal causes each of the radiographic imaging units 102a, 102b, and 102c to start transmitting the entire image. The image transmission is controlled in such a manner that the transmission of the preview image and the transmission of the entire image are prevented from being carried out in an overlapped manner with each other, which can reduce the problem that the image transmission may weigh on the communication capacity. This transmission method is further appropriate especially when the images are transmitted by the wireless communication circuit 160.

The image transmission is not limited thereto, and the radiographic imaging units 102a, 102b, and 102c each may be set to start transmitting the entire image without receiving the signal from outside after transmitting the preview image (the reduced image). For example, in parallel with the processing for generating the reduced image, the FPGA 156 employs image processing such as the noise reduction processing for the entire image, and outwardly transmits the entire image after the processing. This transmission method is useful because it can reduce a time required to transfer the image, when the communication speed is less likely to significantly slow down due to the image transmission weighing on the communication capacity, such as when the wired communication circuit 180 is used.

After that, the CPU 401 of the control apparatus 104 causes the GPU 406 to perform the processing for generating the preview stitched image (a reduced combined image) by stitching the plurality of received preview images. This processing may be performed according to the reception of the plurality of preview images, or may be sequentially started according to reception of partial data of the preview image. Then, the CPU 401 causes this preview stitched image to be displayed on the touch panel monitor 108.

After that, the CPU 401 of the control apparatus 104 causes the GPU 406 to perform the processing for generating the stitched image (the combined image) by stitching the plurality of received radiographic images (the entire images). Then, the CPU 401 causes this stitched image to be displayed on the touch panel monitor 108. In one exemplary embodiment, the CPU 401 is assumed to cause this stitched image to be displayed by replacing the preview stitched image therewith.

Another exemplary embodiment of the present invention will be described with reference to FIG. 8. The meanings of signals or states 1401 to 1415 illustrated in the timing chart are similar to the signals or states 701 to 715 illustrated in FIG. 7, and therefore descriptions thereof will be omitted. Further, the timing chart until the processing for capturing the radiographic images is similar to the example illustrated in FIG. 7, and therefore a description thereof will be omitted.

Figure 8:
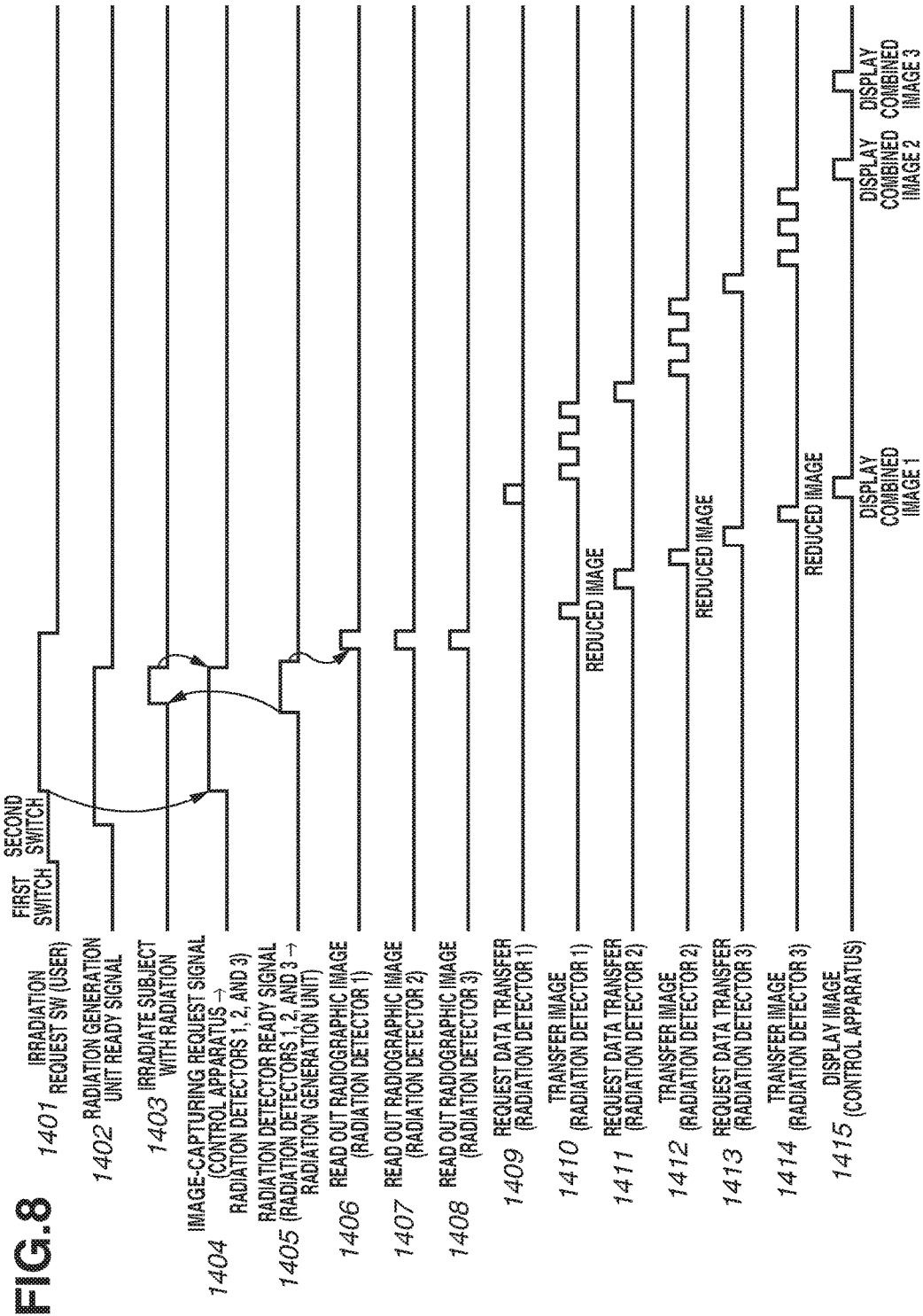
FIG. 8 is a timing chart illustrating a flow of photographing processing and processing for transferring the images according to another exemplary embodiment.

In the example illustrated in FIG. 8, first, the radiographic imaging units (the radiation detectors) 102a, 102b, and 102c transmit the reduced images, and then sequentially transmit the remaining image data after that. For example, the radiographic imaging units 102a, 102b, and 102c each perform thinning-out processing in which one pixel is selected from adjacent 2×2 pixels, thereby generating reduced images quarter in data amount or four divided images. Alternatively, the radiographic imaging units 102a, 102b, and 102c may each generate the reduced images quarter in data amount by thinning-out processing in which four pixels located on a diagonal line extending from an upper left corner to a lower right corner are selected in a square region constituted by 4×4 pixels. In this case, the radiographic imaging units 102a, 102b, and 102c each generate reduced images respectively acquired by selecting four pixels each from the remaining twelve pixels.

The plurality of reduced images (a first reduced image to a fourth reduced image) acquired by the above-described processing are transmitted to the control apparatus 104. The main control circuit 150 controls the wired communication circuit 180 or the wireless communication circuit 160 to transmit the fourth reduced image after transmitting the first reduced image.

The main control circuit 150 first controls the transmission of the preview image. At this time, a single radiographic imaging unit 102 (the radiographic imaging unit 102a in this example) among the plurality of radiographic imaging units 102a, 102b, and 102c starts transmitting the reduced image according to the readout without receiving the specific signal from outside. This single radiographic imaging unit 102a is, for example, specified by the control apparatus 104. As a method for specifying this radiographic imaging unit 102a, the control apparatus 104 specifies the radiographic imaging unit 102a by transmitting a predetermined signal to this single radiographic imaging unit 102a. The radiographic imaging unit 102a that has received this predetermined signal transmits the reduced image without receiving the specific signal, i.e., the signal for requesting the data transfer in the example illustrated in FIG. 8. This specified radiographic imaging unit 102a is subjected to a restriction on transmission of the remaining reduced images, unless receiving the signal for requesting the data transfer. Further, the radiographic imaging units 102*b* and 102*c* that are not the specified radiographic imaging unit 102*a* are subjected to a restriction on the transmission of the image data, unless receiving the signal for requesting the data transfer. This control is performed by the respective main control circuits 150 of the radiographic imaging units 102*a*, 102*b*, and 102*c*.

In the example illustrated in FIG. 8, the radiographic imaging unit 102*a* (the radiation detector 1) transfers the first reduced image, and the control apparatus 104 transmits the signal for requesting the data transfer to the radiographic imaging unit 102*b* (the radiation detector 2) according to completion thereof. This is followed by transmission of the reduced image from the radiographic imaging unit 102*b* according to this signal, transmission of the signal for requesting the data transfer from the control apparatus 104 to the radiographic imaging unit 102*c* (the radiation detector 3), and transmission of the reduced image from the radiographic imaging unit 102*c*, which are carried out sequentially.

With this processing, the transmission of the reduced images from the radiographic imaging units 102*a*, 102*b*, and 102*c* is completed. Then, the CPU 401 of the control apparatus 104 causes the reduced combined image (a combined image 1) generated by combining the plurality of reduced images to be displayed on the touch panel monitor 108. The reduced combined image here may be a reduced stitched image (a preview stitched image) acquired by the processing for positioning the plurality of reduced images based on the image information indicating the overlap region. From the point of view of allowing the user to further quickly check the image, the CPU 401 may be configured to display a combined image generated by positioning the reduced images based on only the above-described layout information without performing the positioning processing based on the image information. In this case, the positioning precision reduces but the image can be further quickly displayed. Alternatively, the CPU 401 may be configured to simply cause the reduced images to be displayed while being arranged with use of the above-described layout information. This method actually eliminates the necessity of the processing for generating the stitched image, thereby allowing the user to further quickly check the image.

In parallel with the generation and the display of this combined image, the control apparatus 104 transmits the signal for requesting the data transfer to the radiographic imaging unit 102*a* (the radiation detector 1). Then, the radiographic imaging unit 102*a* transmits the remaining second to fourth reduced images to the control apparatus 104. Upon completion of the transmission of these second to fourth reduced images to the control apparatus 104, the control apparatus 104 transmits the signal for requesting the data transfer to the radiographic imaging unit 102*b* (the radiation detector 2). Then, the radiographic imaging unit 102*b* transmits the second to fourth reduced images to the control apparatus 104. Further, upon completion of the transmission of these second to fourth reduced images to the control apparatus 104, the control apparatus 104 transmits the signal for requesting the data transfer to the radiographic imaging unit 102*c* (the radiation detector 3). Then, the radiographic imaging unit 102*c* transmits the second to fourth reduced images to the control apparatus 104. With this transmission, the processing for transfer the radiographic images is completed.

The control apparatus (a control unit) 104 generates the radiographic images from the first to fourth reduced images received from the individual radiographic imaging units 102*a*, 102*b*, and 102*c*, and combines these radiographic images to display the combined image.

For example, at this time, the control apparatus 104 causes the combined image acquired by positioning the images with use of only the layout information and no use of the image information to be displayed as a combined image 2 by replacing the combined image 1 therewith, and causes the stitched image acquired by positioning the images based on the image information to be displayed as a combined image 3 by replacing the combined image 2 therewith. Displaying the image in this manner allows the user to acquire the combined image gradually improved in image quality or in positioning precision. Not only the positioning processing but also processing such as the processing for reducing the number of structure images and processing for reducing scattered radiation may be omitted for the combined image 1 or 2, and these processing procedures may be employed for the combined image 3, which allows the user to quickly check the image. Alternatively, the control apparatus 104 can also be configured to perform the processing for reducing the number of structure images during the processing for acquiring the combined images 1 to 3, and perform the positioning processing and the processing for reducing the scattered radiation only for the combined images 2 and 3, from the point of view of preventing an inappropriate image from being presented to a technician even only temporarily.

In one exemplary embodiment, the control apparatus 104 employs the positioning processing for the combined image 1, and uses a positional shift amount among the individual reduced images that is acquired during the course of this positioning processing for the positioning processing for generating the combined image 2 or the combined image 3. This method can speed up the positioning processing and lead to a further quick display of the stitched image.

Further, in another exemplary embodiment, the control apparatus 104 transmits a specific signal for causing each of the radiographic imaging units 102*a*, 102*b*, and 102*c* to start transmitting the third reduced image to each of the plurality of radiographic imaging units 102*a*, 102*b*, and 102*c* upon the completion of the transmission of the second reduced image from each of the plurality of radiographic imaging units 102*a*, 102*b*, and 102*c*. Then, in this case, the control apparatus 104 can speed up the processing for generating the combined image 2, if the combined image 2 is generated based on the first and second reduced images and the third image is generated based on the entire images.

In another exemplary embodiment, the plurality of radiographic imaging units 102*a*, 102*b*, and 102*c* is controlled to individually transmit the radiographic images concurrently in parallel with one another. In this case, the control apparatus 104 is assumed to specify one of the plurality of radiographic imaging units 102*a*, 102*b*, and 102*c* that transmit the radiographic images concurrently in parallel with one another, and reduce a rate at which the image is transmitted with respect to the radiographic imaging units 102 other than the specified radiographic imaging unit 102. This method can cause the radiographic imaging units 102*a*, 102*b*, and 102*c* to transmit the images concurrently in parallel with each other while allowing the image transmission to less weigh on the communication capacity, thereby reducing the time required for the processing for transferring the image.

Figure 9:
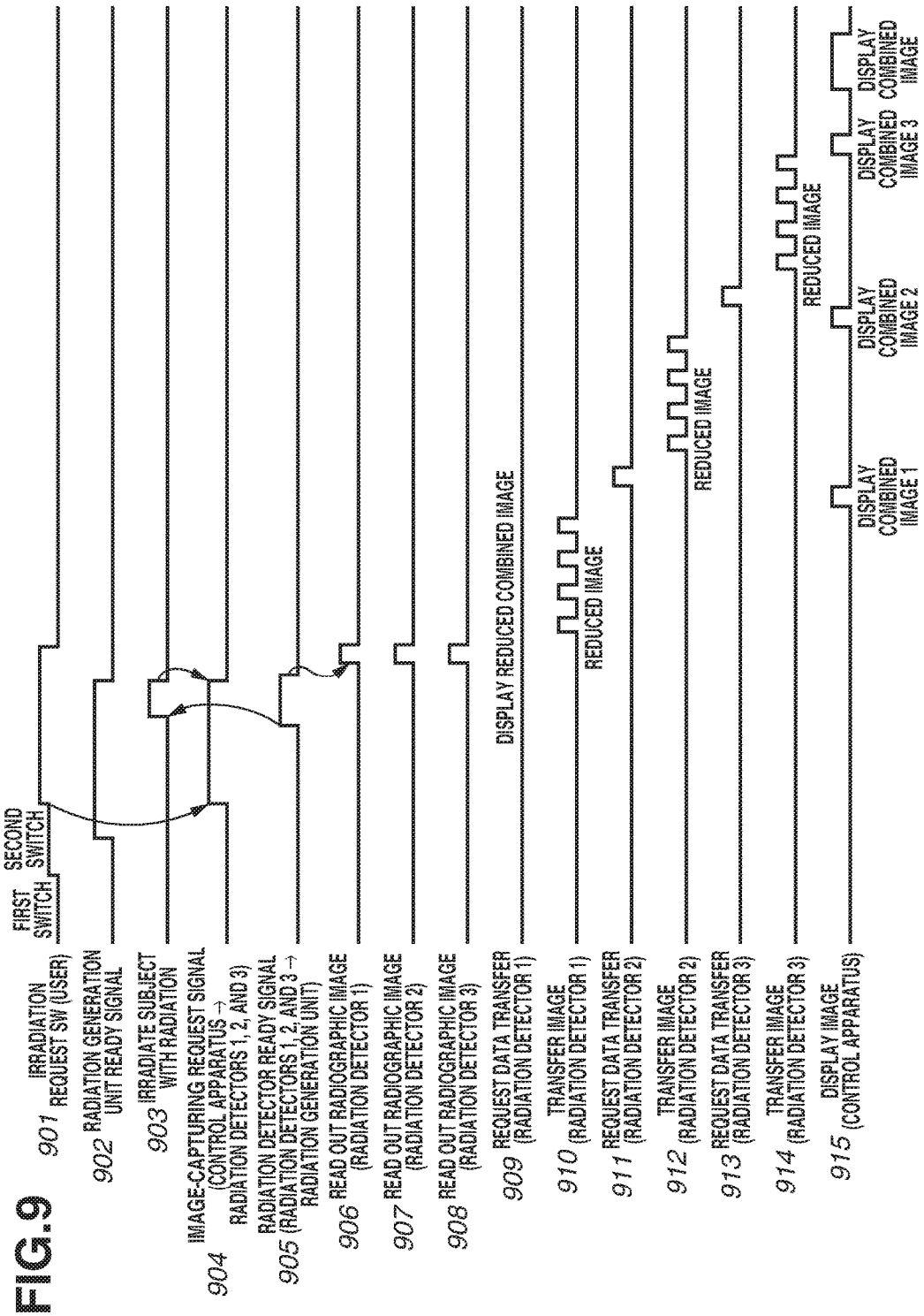
FIG. 9 is a timing chart illustrating a flow of photographing processing and processing for transferring the images according to another exemplary embodiment.

In the example illustrated in FIG. 9, the transmission of the first to fourth reduced images from the radiographic imaging unit 102*a* (the radiation detector 1), the transmission of the first to fourth reduced images from the radiographic imaging unit 102b (the radiation detector 2), and the transmission of the first to fourth reduced images from the radiographic imaging unit 102c (the radiation detector 3) are carried out sequentially in a time-sharing manner. This control is performed by the specific signal (the signal for requesting the data transfer) from the control apparatus 104, and the radiographic imaging units 102a, 102b, and 102c that control the transmission of the reduced images based on this signal, similarly to the examples illustrated in FIGS. 7 and 8. In this example, the CPU 401 of the control apparatus 104 sequentially displays the entire image of the radiographic imaging unit 102a, the entire image of the radiographic imaging unit 102b, and the entire image of the radiographic imaging unit 102c, and then displays the stitched image thereafter. This method is convenient if the user checks the image in an order of checking the stitched image for each partial region and then checking the stitched image of the entire region thereafter. Alternatively, this method allows a partial image that the user is most interested in to be displayed prior to the other partial images according to the image-capturing site to be captured by the stitch imaging. In this case, the control apparatus 104 can achieve this display by, for example, controlling the radiographic imaging units 102a, 102b, and 102c with use of the above-described specific signal in such a manner that the radiographic imaging units 102a, 102b, and 102c transmit the radiographic images in an order specified by the control apparatus 104 in advance.

The processing procedures for transferring the images described above with reference to FIGS. 7 to 9 allow the images to be transferred appropriately for a situation, provided that the control apparatus 104 is configured to specify which processing procedure should be performed.

Figure 10:
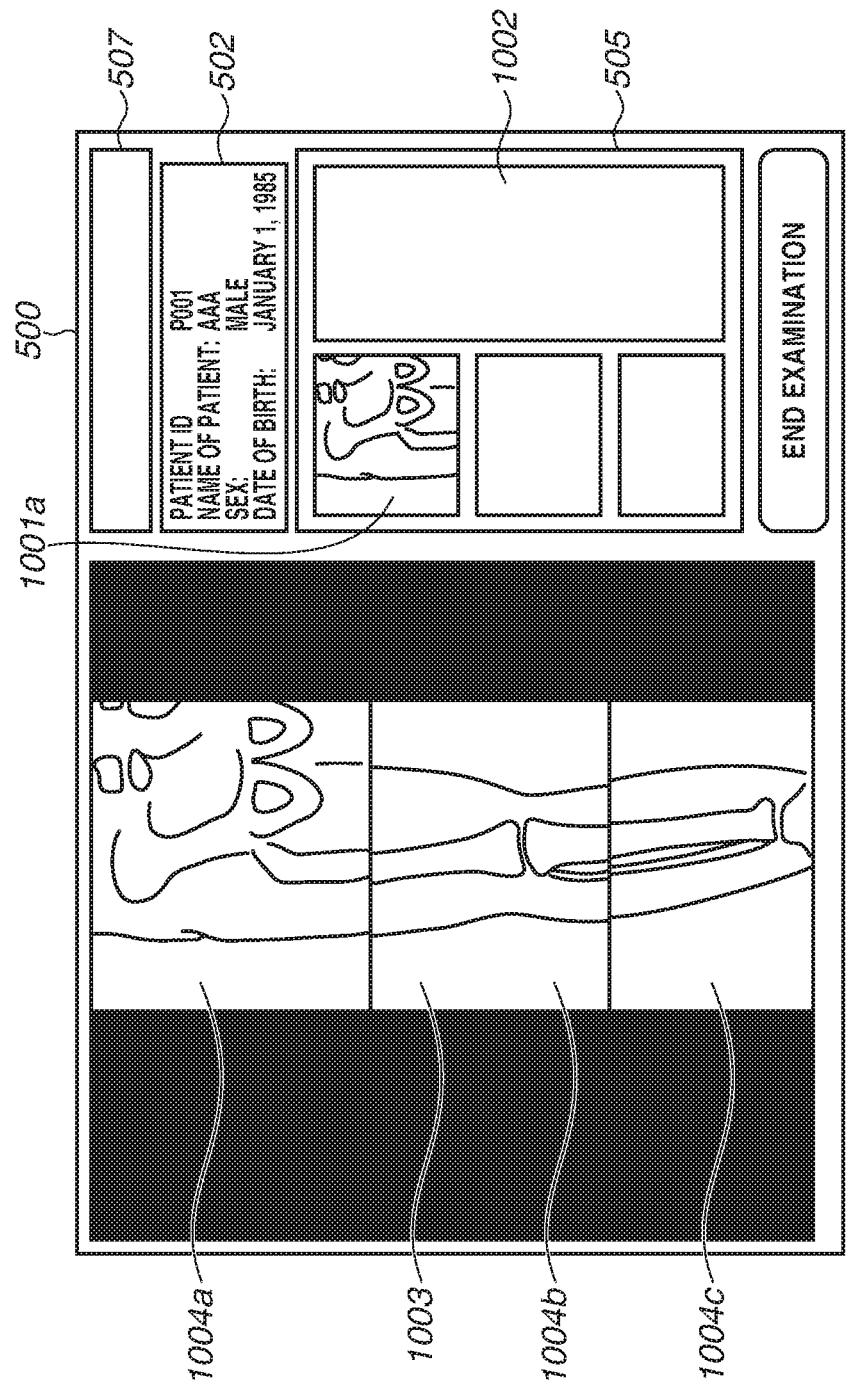
FIG. 10 illustrates an example of a display screen according to the exemplary embodiment.

Examples of the display of the display screen 500 will be described with reference to FIGS. 10 and 11. An image 1003, which is referred to as the combined image 1 in FIG. 8, is displayed in the example illustrated in FIG. 10, and an image 1103, which is referred to as the combined image 2 in FIG. 8, is displayed in the example illustrated in FIG. 11. Features also illustrated in FIG. 5 will not be described below. In FIG. 10, first to third thumbnail areas 1001a, 1001b, and 1001c and a long-scale thumbnail area 1002 are provided in the area where the image-capturing information 505 is displayed.

The image 1003, which corresponds to the combined image 1, is displayed on the display screen 500 illustrated in FIG. 10, and this example is a display with the first to fourth reduced images received from the radiographic imaging unit 102a. In this case, a thumbnail is displayed only in the first thumbnail area 1001a among the thumbnail areas 1001a, 1001b, and 1001c respectively corresponding to the radiographic imaging units 102a, 102b, and 102c in the area corresponding to a certain image-capturing condition in the image-capturing information 505. No thumbnail is displayed in the second and third thumbnail areas 1001b and 1001c and the long-scale thumbnail area 1002. In this manner, the control apparatus 104 is assumed to cause the thumbnail not to be displayed in the thumbnail area when the entire image is not received, i.e., not all of the first to fourth reduced images are received, and cause the thumbnail to be displayed in the thumbnail area upon reception of the entire image. The control apparatus 104 controls the display of the thumbnail area according to a progress of the reception of the radiographic images in this manner, which allows the user to check the progress of the reception of the images from each of the radiographic imaging units 102a, 102b, and 102c from the display of the image-capturing information 505. Then, if the control apparatus 104 is configured to cause the thumbnail of the stitched image to be displayed in the long-scale thumbnail area 1002 upon completion of the processing for generating the stitched image, this allows the user to check a progress of the processing for generating the stitched image from the display of the image-capturing information 505.

In the example illustrated in FIG. 10, a first image 1004a corresponding to the reduced image from the radiographic imaging unit 102a, a second image 1004b corresponding to the reduced image from the radiographic imaging unit 102b, and a third image 1004c corresponding to the reduced image from the radiographic imaging unit 102c are displayed based on the layout information as the image 1003, which corresponds to the combined image 1. At this stage, the positioning processing based on the image information is not performed. At this time, the partial images 1004a, 1004b, and 1004c respectively corresponding to the radiographic imaging units 102a, 102b, and 102c are individually selectably displayed. Then, according to a selection by an operation input, the partial image specified by this selection is displayed in an enlarged manner.

Figure 11:
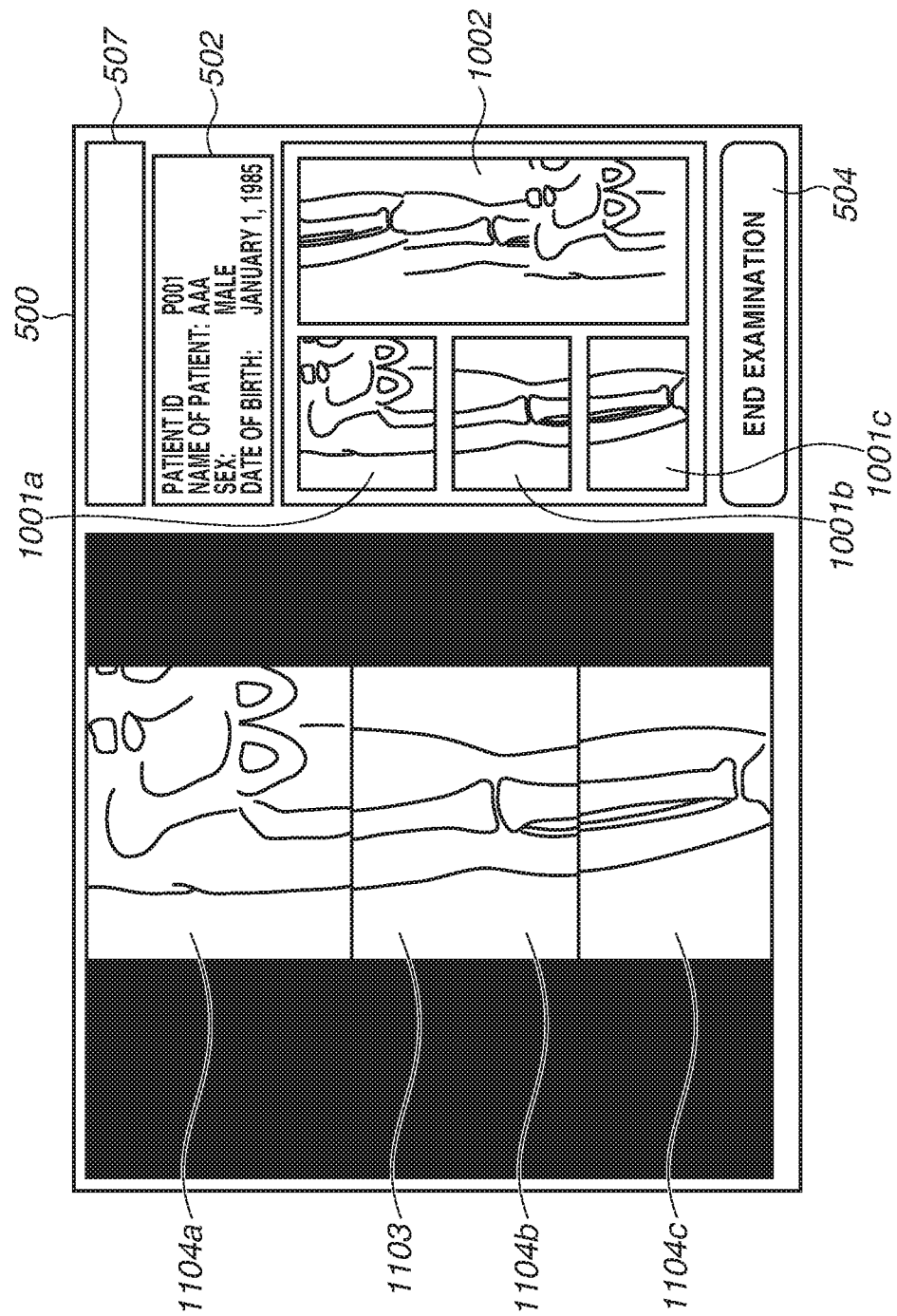
FIG. 11 illustrates an example of a display screen according to the exemplary embodiment.

The image 1103, which corresponds to the combined image 2, is displayed on the screen illustrated in FIG. 11, and this example is the display screen 500 with the first to fourth reduced images received from each of the individual radiographic imaging units 102a, 102b, and 102c. In this case, thumbnails are displayed in the first to third thumbnail areas 1001a, 1001b, and 1001c, respectively, and the thumbnail of the stitched image is displayed in the long-scale thumbnail area 1002. Further, in the example illustrated in FIG. 11, the stitched image acquired by the positioning processing based on the image information is displayed as the image 1103, which corresponds to the combined image 2.

The control apparatus 104 may be configured to cause the thumbnail to be displayed in the long-scale thumbnail area 1002, when the reduced images are received as far as the first and second reduced images, and the reduced stitched image based on the first and second reduced images is generated. This is because, in a case where a resolution of a display device used for the display of the image is lower than the number of pixels in the entire image, the entire image cannot be displayed pixel by pixel without enlargement processing performed thereon. In this case, the stitched image based on the entire image is used as the image to be transferred to the PACS 155, and the reduced stitched image is used as the image to be displayed on the touch panel monitor 108.

A configuration of a stitch imaging system according to the present exemplary embodiment will be described with reference to FIG. 12. In this system, the radiographic imaging units 102a, 102b, and 102c each communicate with the control apparatus 104 using the wireless communication circuit 160. The radiographing system includes the control apparatus 104, the platform 101, and the plurality of portable type radiographic imaging units 102a, 102b, and 102c as described above. The platform connectors 206a, 206b, and 206c are replaced with a wireless AP 1201 connected to the relay (a network hub) 103, for example, in a wired manner.

The radiographic imaging unit 102 includes the wireless communication circuit 160 together with the radiographic imaging unit connector 107 for connecting the wired communication circuit 180 to outside. At the time of the wireless configuration, the wireless communication circuit 160 of the radiographic imaging unit 102 is connected to the relay 103 via the wireless AP 1201, and is then connected to the control apparatus 104. As a result, the wireless network including the individual radiographic imaging units 102*a*, 102*b*, and 102*c* and the control apparatus 104 is created.

In the case of the wireless network configuration, there is communication from the wireless communication circuit 160 to the wireless AP 1201 between the radiographic imaging unit 102 and the control apparatus 104, whereby the image transfer speed may slow down due to the communication speed therebetween or the image transfer may end up in a failure. On the other hand, in the case of the wired network configuration such as the configuration illustrated in FIG. 2, the radiographic imaging unit 102 and the control apparatus 104 are directly connected to the relay 103 in a wired manner via the Ethernet (registered trademark) cables 205 between the radiographic imaging unit 102 and the control apparatus 104, which leads to a generously high communication speed including some extra.

Figure 2:
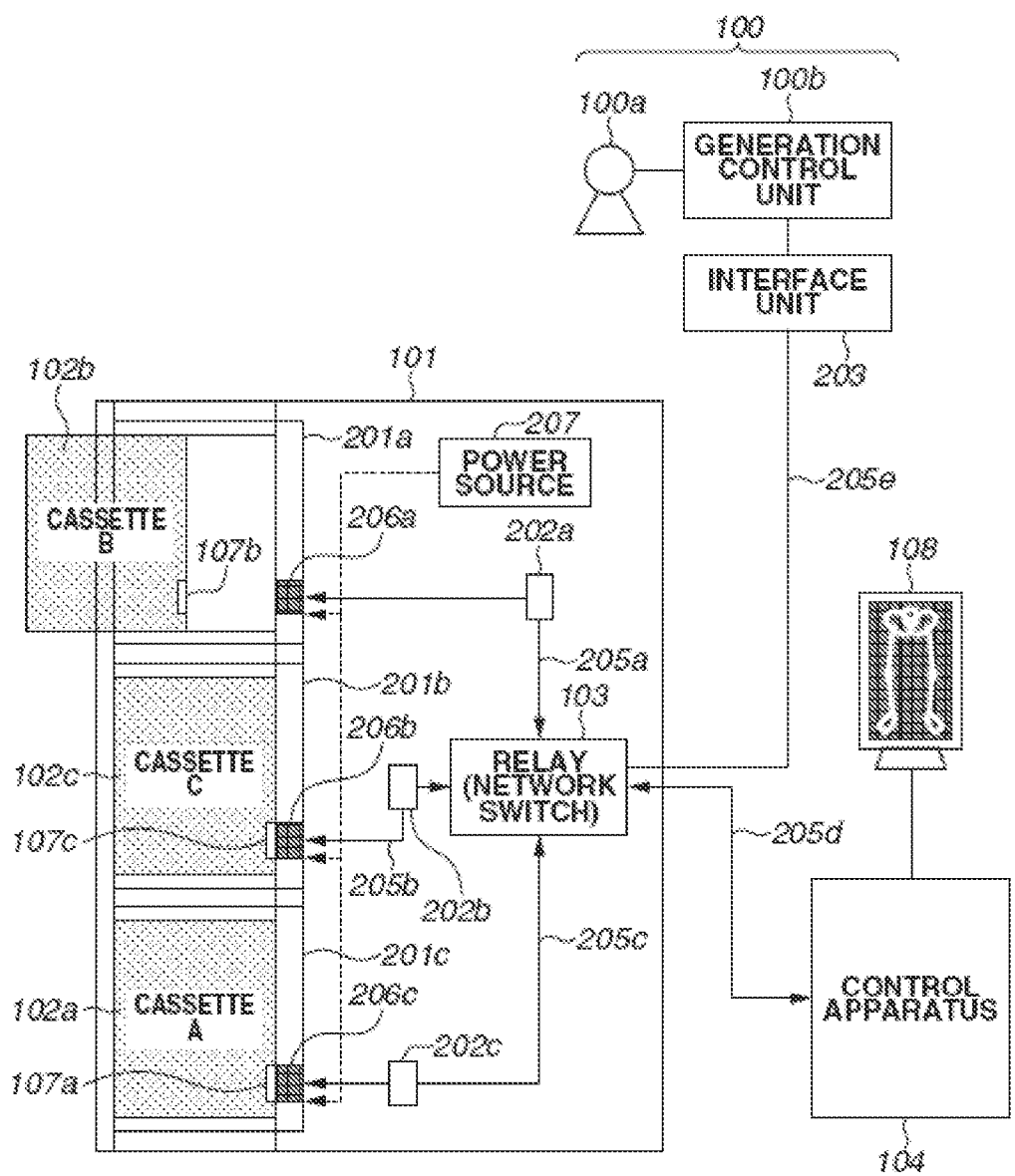
FIG. 2 is a block diagram illustrating a configuration of a stitch imaging system according to the exemplary embodiment.

Therefore, in one exemplary embodiment, in the case of the wired network configuration such as the configuration illustrated in FIG. 2, the individual radiographic imaging units 102*a*, 102*b*, and 102*c* transmit the radiographic images to the control apparatus 104 simultaneously, as soon as they acquire the radiographic images. On the other hand, in the case of the wireless network configuration such as the configuration illustrated in FIG. 12, the radiographic imaging unit 102*a*, the radiographic imaging unit 102*b*, and the radiographic imaging unit 102*c* transmit the radiographic images to the control apparatus 104 in, for example, this order sequentially in the time-sharing manner, after the individual radiographic imaging units 102*a*, 102*b*, and 102*c* acquire the radiographic images.

Figure 12:
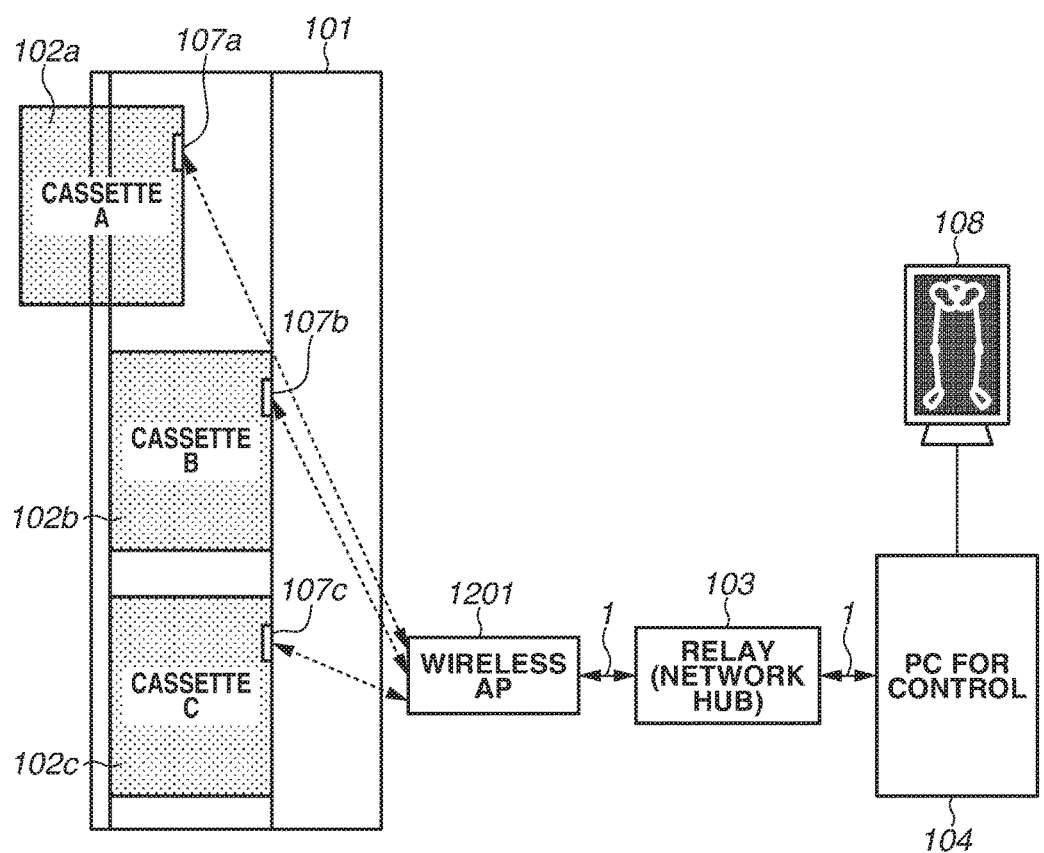
FIG. 12 is a block diagram illustrating a different configuration of a radiographing system according to an exemplary embodiment.

For example, the control apparatus 104 determines whether the stitch imaging system is a system using the wired network such as the system illustrated in FIG. 2, or a system using the wireless network such as the system illustrated in FIG. 12, and performs control of switching the method for transmitting the radiographic images according to the determination.

Not all of the radiographic imaging units 102*a*, 102*b*, and 102*c* have to communicate by the same communication method. For example, the radiographic imaging units 102*a*, 102*b*, and 102*c* may be set in such a manner that the radiographic imaging unit 102*a* communicates in a wired manner while the radiographic imaging units 102*b* and 102*c* communicate wirelessly. In this case, the control apparatus 104 transmits the signals for requesting the data transfer to the radiographic imaging units 102*b* and 102*c* to control the timings at which the images are transmitted. On the other hand, a different transmission method from the radiographic imaging units 102*b* and 102*c* is specified for the radiographic imaging unit 102*a*. The radiographic imaging unit 102*a* causes the wired communication circuit 180 to transmit the radiographic image according to the readout of the image signals and the generation of the digital radiographic image signals independently of the reception of the signal for requesting the data transfer.

Figure 13:
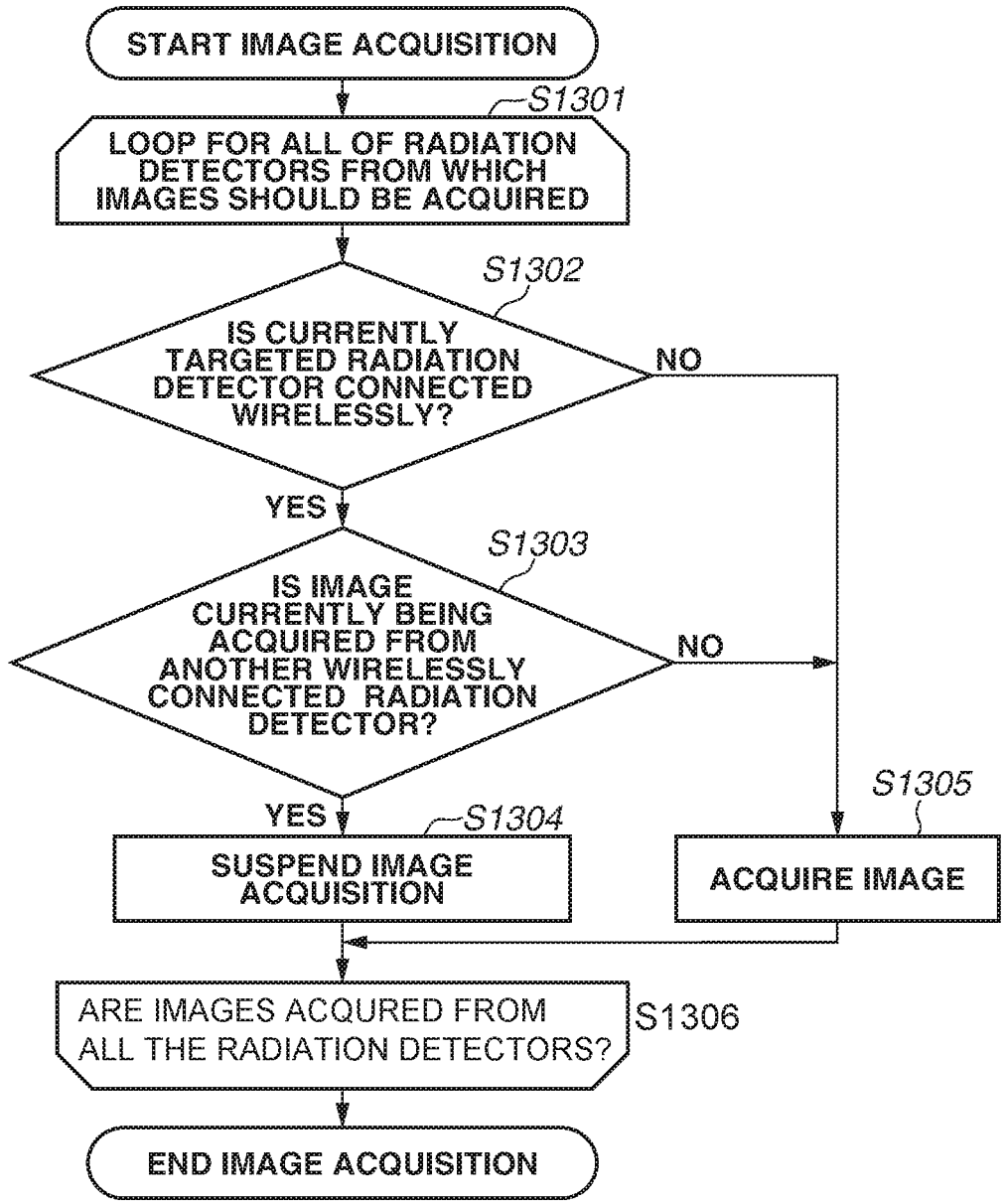
FIG. 13 is a flowchart illustrating a flow of processing for transferring the images according to the exemplary embodiment.

A flow of processing for receiving the radiographic images that is performed by the control apparatus 104 will be described with reference to a flowchart illustrated in FIG. 13. This processing is processing corresponding to step S607 (TRANSFER IMAGES) illustrated in FIG. 6. In step S1301, the control apparatus 104 starts the processing for acquiring the radiographic images from the radiographic imaging units 102*a*, 102*b*, and 102*c* (steps S1301 to S1305).

In step S1302, the CPU 401 of the control apparatus 104 determines whether the currently targeted radiographic imaging unit 102 is connected to the control apparatus 104 in a wired manner, or connected to the control apparatus 104 wirelessly with use of the wireless access point 1201. The CPU 401 makes this determination by referring to a MAC address contained in a signal from the radiographic imaging unit 102, because a MAC address of the wired communication circuit 180 and a MAC address of the wireless communication circuit 160 are different from each other.

If the CPU 401 determines that the currently targeted radiographic imaging unit 102 is connected in a wired manner in step S1302 (NO in step S1302), in step S1305, the control apparatus 104 acquires the image from the currently targeted radiographic imaging unit 102. If the CPU 401 determines that the currently targeted radiographic imaging unit 102 is connected wirelessly in step S1302 (YES in step S1302), in step S1303, the CPU 401 determines whether the control apparatus 104 is currently in the process of acquiring the image from another wirelessly connected radiographic imaging unit 102.

If the CPU 401 determines that the control apparatus 104 is not currently in the process of acquiring the image from another wirelessly connected radiographic imaging unit 102 in step S1303 (NO in step S1303), in step S1305, the control apparatus 104 causes the second NIC 405*b* to transmit the signal for requesting the data transfer to the radiographic imaging unit 102. In step S1305, this transmission leads to the control apparatus 104 acquiring the image from the currently targeted radiographic imaging unit 102.

In step S1303, if the CPU 401 determines that the control apparatus 104 is currently in the process of acquiring the image from another wirelessly connected radiographic imaging unit 102 (YES in step S1303), then in step S1304, the control apparatus 104 suspends the image acquisition from the currently targeted radiographic imaging unit 102. Then, in step S1305, the control apparatus 104 acquires the image from the currently targeted radiographic imaging unit 102 successively as soon as the control apparatus 104 completes the image acquisition from the other radiographic imaging unit 102. In the step S1306, the control apparatus 104 checks if the control apparatus receives radiographic images from all the radiographic imaging units. If there is still a radiographic imaging unit which has not yet transmitted radiographic image, the processing goes back to the step S1301. If the control apparatus 104 acquires all the radiographic imaging units, the processing for receiving the radiographic images illustrated in FIG. 6 ends. This processing allows the control apparatus 104 to perform control of paralleling the processing for transferring the image within a range that can prevent the image transmission from weighing on the communication capacity, thereby reducing the time required for the image transfer.

According to the above-described exemplary embodiments, the preview image small in data amount is transmitted from each of the radiographic imaging units 102*a*, 102*b*, and 102*c* included in the stitch imaging system prior to the entire radiographic image, which allows the user to quickly check a result of the image-capturing, thereby relieving discomfort of the subject.

In the above-described exemplary embodiments, the radiographic imaging units 102*a*, 102*b*, and 102*c* are each assumed to transmit the preview image smaller in data amount than the radiographic image acquired from the image-capturing, and then transmit the image that contains the remaining data (the entire image or the second to fourth reduced images) thereafter, but are not limited thereto. For example, the radiographic imaging units 102*a*, 102*b*, and 102*c* may be each configured to transmit the radiographic image without generating the preview image.

The control apparatus 104 in the above-described exemplary embodiments is a single apparatus. However, in another exemplary embodiment, the functions of this image-capturing control apparatus 104 are realized by a control system including a plurality of information processing apparatuses. In this case, the plurality of information processing apparatuses each includes a communication circuit, and is communicable with one another by this communication circuit. One of the plurality of information processing apparatuses can be configured to function as an image processing unit that generates the stitched image, and another apparatus can be configured to function as a control unit. This plurality of information processing apparatuses only has to be communicable at a predetermined communication rate, and does not have to be set up in a same hospital facility or a same country. Further, this control system can also be configured to use, for example, a server apparatus or a server group shared among a plurality of control systems as the image processing unit.

Further, exemplary embodiments of the present invention also include an exemplary embodiment in which a program of software capable of realizing the functions of the above-described exemplary embodiments is supplied to a system or an apparatus, and a computer of the system or apparatus reads out and executes a code of this supplied program.

Therefore, the program code itself installed in this computer for realizing the processing according to the exemplary embodiments by the computer is also one exemplary embodiment of the present invention. Further, an operating system (OS) or the like running on the computer partially or entirely performs the actual processing based on an instruction contained in the program read out by the computer, and the functions of the above-described exemplary embodiments can also be realized by this processing.

An exemplary embodiment constructed by arbitrarily combining the above-described exemplary embodiments is also included in the exemplary embodiments of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-017885, filed Jan. 30, 2015, which is hereby incorporated by reference herein in its entirety.

What is claimed is:

1. A radiographing apparatus usable for stitch imaging, the radiographing apparatus comprising:
a plurality of radiation sensors including a first radiation sensor and a second radiation sensor configured to acquire radiographic image signals by detecting radiation, wherein each of the first radiation sensor and the second radiation sensor has a readout circuit configured to read out the radiographic image signals and a communication circuit configured to output a digital radiographic image based on the radiographic image signals;
a memory storing a program; and
one or more processors which, by executing the program, function as:
a control unit configured to control the plurality of radiation sensors,
wherein, based on the digital radiographic image from the first radiation sensor being received by the control unit, the control unit outputs a specific signal to the second radiation sensor for requesting the second radiation sensor to output the digital radiographic image to the control unit based on the specific signal.

2. The radiographing apparatus according to claim 1, wherein the communication circuit of the second radiation sensor does not output the digital radiographic image until a reception of the specific signal after the readout circuit of the second radiation sensor reads out the radiographic image signals.

3. The radiographing apparatus according to claim 1, wherein each of the first radiation sensor and the second radiation sensor is configured to generate a plurality of reduced images of the digital radiographic image.

4. The radiographing apparatus according to claim 3, wherein the first radiation sensor generates the plurality of the reduced images of the digital radiographic image after the readout circuit of the first radiation sensor reads out the radiographic image signals, and the control unit outputs the specific signal to the second radiation sensor based on that the plurality of reduced images of the digital radiographic image is output from the first radiation sensor.

5. The radiographing apparatus according to claim 3, wherein the second radiation sensor generates the plurality of reduced images of the digital radiographic image based on that the specific signal has been received.

6. The radiographing apparatus according to claim 1, wherein the communication circuit of each of the first radiation sensor and the second radiation sensor is configured to output the digital radiographic image using wireless communication.

7. The radiographing apparatus according to claim 1, wherein the one or more processors executing the program further function as a display control unit to display a stitched image, which is acquired by stitching digital radiographic images acquired from the first radiation sensor and the second radiation sensor, to be displayed based on a reception of the digital radiographic images by the control unit.

8. The radiographing apparatus according to claim 7, wherein the display control unit is configured to cause a display unit to display the stitched image and thumbnails of the stitched image.

9. The radiographing apparatus according to claim 1, wherein the control unit restricts transmission of the digital radiographic image from the second radiation sensor until a reception of the specific signal from the control unit after completion of transmission of the digital radiographic image from the first radiation sensor.

10. The radiographing apparatus according to claim 1, wherein the control unit controls the second radiation sensor such that the communication circuit of the second radiation sensor starts transmitting a preview image after the readout circuit of the second radiation sensor reads out the radiographic image signals, and causes the communication circuit of the second radiation sensor to start outputting the digital radiographic image in response to a reception of the specific signal after a completion of a transmission of the preview image.

11. A stitch imaging system comprising:
a plurality of radiation sensors including a first radiation sensor and a second radiation sensor configured to acquire radiographic image signals by detecting radiation, wherein each of the first radiation sensor and the second radiation sensor has a readout circuit configured to read out the radiographic image signals and a communication circuit configured to output a digital radiographic image based on the radiographic image signals;
a memory storing a program; and one or more processors which, by executing the program, function as:
a control apparatus configured to control the plurality of radiation sensors,
wherein, based on the digital radiographic image from the first radiation sensor being received by the control apparatus, the control apparatus outputs a specific signal to the second radiation sensor for requesting the second radiation sensor to output the digital radiographic image to the control apparatus based on the specific signal.

12. The stitch imaging system according to claim 11, wherein the one or more processors executing the program further function as a display control unit to display a stitched image, which is acquired by stitching digital radiographic images acquired from the first radiation sensor and the second radiation sensor, to be displayed based on a reception of the digital radiographic images by the control apparatus.

13. The stitch imaging system according to claim 12, wherein the display control unit is configured to cause a display unit to display the stitched image and thumbnails of the stitched image.

14. The stitch imaging system according to claim 11, wherein the control apparatus outputs a specific signal to the first radiation sensor according to irradiation with radiation emitted toward the plurality of radiation sensors simultaneously, and
wherein the control apparatus outputs the specific signal to the second radiation sensor according to a completion of a reception of the digital radiographic image by the control apparatus.

15. The stitch imaging system according to claim 11, wherein the control apparatus is configured to control communication between the control apparatus and the plurality of radiation sensors to prevent carrying out of a simultaneous transmission of the digital radiographic image from the first radiation sensor and the digital radiographic image from the second radiation sensor.

16. A stitch imaging system comprising:
a plurality of radiation sensors including a first radiation sensor and a second radiation sensor configured to acquire radiographic image signals by detecting radiation, wherein each of the first radiation sensor and the second radiation sensor has a readout circuit configured to read out the radiographic image signals and a communication circuit configured to output a digital radiographic image based on the radiographic image signals;
a memory storing a program; and
one or more processors which, by executing the program, function as:
a control unit configured to control the plurality of radiation sensors to receive the digital radiographic image from the communication circuit of each of the first radiation sensor and the second radiation sensor according to irradiation of radiation emitted toward the plurality of radiation sensors,
wherein, based on the digital radiographic image from the first radiation sensor being received by the control unit, the control unit outputs a specific signal to the second radiation sensor for requesting the second radiation sensor to output the digital radiographic image to the control unit based on the specific signal.

17. A method for controlling a stitch imaging system having a control apparatus, and a plurality of radiation sensors including a first radiation sensor and a second radiation sensor, wherein each of the first radiation sensor and the second radiation sensor has a readout circuit configured to read out radiographic image signals, and a communication circuit configured to output a digital radiographic image based on the radiographic image signals, the method comprising:
acquiring radiographic image signals by detecting radiation with use of the first radiation sensor and the second radiation sensor; and
controlling the plurality of radiation sensors,
wherein, based on the digital radiographic image from the first radiation sensor being received by the control apparatus, controlling the plurality of radiation sensors includes outputting a specific signal to the second radiation sensor for requesting the second radiation sensor to output the digital radiographic image to the control apparatus based on the specific signal.

18. A method for controlling a stitch imaging system having a plurality of radiation sensors including a first radiation sensor and a second radiation sensor configured to acquire radiographic image signals by detecting radiation, wherein each of the first radiation sensor and the second radiation sensor has a readout circuit configured to read out the radiographic image signals, and a communication circuit configured to output a digital radiographic image based on the radiographic image signals, the method comprising:
controlling the plurality of radiation sensors to receive the digital radiographic image from the communication circuit of each of the first radiation sensor and the second radiation sensor according to irradiation of radiation emitted toward the plurality of radiation sensors,
wherein, based on the digital radiographic image from the first radiation sensor being received, controlling the plurality of radiation sensors includes outputting a specific signal to the second radiation sensor for requesting the second radiation sensor to output the digital radiographic image based on the specific signal.

19. A non-transitory computer-readable storage medium storing a program causing a computer to perform the method according to claim 17.

20. A non-transitory computer-readable storage medium storing a program causing a computer to perform the method according to claim 18.

21. A method for controlling a radiographing apparatus usable for stitch imaging, wherein the radiographing apparatus includes a plurality of radiation sensors including a first radiation sensor and a second radiation sensor, wherein each of the first radiation sensor and the second radiation sensor has a readout circuit configured to read out radiographic image signals, and a communication circuit configured to output a digital radiographic image based on the radiographic image signals, the method comprising:
acquiring radiographic image signals by detecting radiation with use of the first radiation sensor and the second radiation sensor: and
controlling the plurality of radiation sensors by a control unit,
wherein, based on the digital radiographic image from the first radiation sensor being received, controlling the plurality of radiation sensors includes outputting a specific signal to the second radiation sensor for requesting the second radiation sensor to output the digital radiographic image to the control unit based on the specific signal.

* * * * *